United States Patent
Zwirn

(10) Patent No.: US 9,451,932 B2
(45) Date of Patent: Sep. 27, 2016

(54) CLUTTER SUPPRESSION IN ULTRASONIC IMAGING SYSTEMS

(75) Inventor: Gil Zwirn, Petach Tikva (IL)

(73) Assignee: CrystalView Medical Imaging Limited, Channel Islands (GB)

(*) Notice: Subject to any disclaimer, the term of this patent is extended or adjusted under 35 U.S.C. 154(b) by 968 days.

(21) Appl. No.: 13/408,136

(22) Filed: Feb. 29, 2012

(65) Prior Publication Data

US 2012/0157851 A1   Jun. 21, 2012

Related U.S. Application Data

(63) Continuation-in-part of application No. 13/234,927, filed on Sep. 16, 2011, now abandoned, which is a continuation-in-part of application No. 11/722,246, filed as application No. PCT/IL2005/001383 on Dec. 27, 2005, now Pat. No. 8,045,777.

(60) Provisional application No. 60/640,368, filed on Dec. 30, 2004.

(51) Int. Cl.
*A61B 8/00* (2006.01)
*G01S 7/52* (2006.01)
*A61B 8/08* (2006.01)

(52) U.S. Cl.
CPC .......... *A61B 8/4488* (2013.01); *A61B 8/5207* (2013.01); *G01S 7/52047* (2013.01); *G01S 7/52077* (2013.01); *A61B 8/0883* (2013.01)

(58) Field of Classification Search
None
See application file for complete search history.

(56) References Cited

U.S. PATENT DOCUMENTS

| | | | |
|---|---|---|---|
| 5,457,754 A | 10/1995 | Han | |
| 6,126,604 A | 10/2000 | Bae | |
| 6,251,074 B1 | 6/2001 | Averkiou et al. | |
| 6,705,993 B2 | 3/2004 | Ebbini et al. | |
| 6,716,175 B2 | 4/2004 | Geiser | |
| 8,045,777 B2 | 10/2011 | Zwirn | |

(Continued)

FOREIGN PATENT DOCUMENTS

| JP | 09164138 A | 6/1997 |
|---|---|---|
| WO | 03079037 A2 | 9/2003 |

(Continued)

OTHER PUBLICATIONS

Mishra et al., entitled "A GA based approach for boundary detection of left ventricle with echocardiographic image sequences," Image and Vision Computing, vol. 21, 2003, pp. 967-976.

(Continued)

*Primary Examiner* — Patricia Park
(74) *Attorney, Agent, or Firm* — Symbus Law Group LLC; Clifford D. Hyra

(57) ABSTRACT

A method of ultrasound imaging is provided herein. The method includes the following stages: transmitting ultrasound radiation towards a target and receiving reflections of the ultrasound radiation from a region of the target in a main reflected signal and one or more auxiliary reflected signals, wherein each one of the reflected signals comprises an input dataset and is associated with a beam with a different and distinct beam pattern; compounding the input datasets from the main reflected signal and one or more auxiliary reflected signals, by the use of a compounding function, said compounding function using parameters derived from spatial analysis of the input datasets.

24 Claims, 3 Drawing Sheets

(56) References Cited

U.S. PATENT DOCUMENTS

2003/0210179 A1 11/2003 Dizaji et al.
2008/0262352 A1 10/2008 Zwirn
2009/0141957 A1 6/2009 Yen et al.

FOREIGN PATENT DOCUMENTS

WO  2006070362 A2  7/2006
WO  WO 2006/070362 A2  7/2006

OTHER PUBLICATIONS

P. D. Krishna, P. M. Shankar, and V. L. Newhouse; Subharmonic generation from ultrasonic contrast agents, Physics in Medicine and Biology, vol. 44, 1999, pp. 681-694.
Kirk T. Spencer, MD, James Bednarz, BD, Patrick G. Rafter, MS, Claudia Korcarz, DVM, and Robert M. Lang MD, Use of Harmonic Imaging without Echocardiographic Contrast to Improve Two-Dimensional Image Quality, American Journal of Cardiology, vol. 82, 1998, pp. 794-799.
Gil Zwirn and Solange Akselrod, Stationary Clutter Rejection in Echocardiography, Ultrasound in Medicine and Biology, vol. 32, 2006, pp. 43-52.
Alan Herment, Guy Demoment, and Philippe Dumee, Improved Estimation of Low Velocities in Color Doppler Imaging by Adapting the Mean Frequency Estimator to the Clutter Rejection Filter, IEEE Transactions on Biomedical Engineering, vol. 43, 1996, pp. 919-927.
Alfonso Farina, Antenna-based signal processing techniques for radar systems, Chapter 4, Sidelobe Canceler (SLC) system, 4.1 Introduction and working principle of SLC, pp. 95-103.
Written Opinion of the International Searching Authority published Jun. 30, 2007 for PCT/IL2005/001383 filed Dec. 27, 2005.
International Preliminary Report on Pantentability published Jul. 3, 2007 published Jun. 30, 2007 for PCT/IL2005/001383 filed Dec. 27, 2005.
International Search report published Mar. 8, 2007 for PCT/IL2005/001383 filed Dec. 27, 2005.
European Search Report for the corresponding European application No. 05819236.0 completed on May 18, 2010.
Office Action issued Oct. 6, 2010 for U.S. Appl. No. 11/722,246, filed Jun. 20, 2007.
Response to Office Action filed Mar. 7, 2011 for Office Action issued Oct. 6, 2010 for U.S. Appl. No. 11/722,246, filed Jun. 20, 2007.
Notice of Allowance issued May 26, 2011 for U.S. Appl. No. 11/722,246, filed Jun. 20, 2007.
Office Action issued on Jun. 26, 2011 for corresponding Japanese application No. 2007-548960.
Letter dated Jun. 21, 2011 from Japanese associate to client providing a brief explanation of Examiners objections raised in Office Action issued Jun. 26, 2011 for corresponding Japanese application No. 2007-548960.
Zwirn Gil et al., entitled "Stationary clutter rejection in echocardiography". Ultrasound in Medicine and Biology, New York, US, vol. 32, No. 1, Jan. 1, 2006, pp. 43-52.
International Search Report dated Sep. 9, 2013.

CLUTTER SUPPRESSION IN ULTRASONIC IMAGING SYSTEMS

This application is a continuation-in-part of U.S. patent application Ser. No. 13/234,927 filed on Sep. 16, 2011, which in turn claimed priority from U.S. patent application Ser. No. 11/722,246 filed on Jun. 20, 2007, now U.S. Pat. No. 8,045,777, issued 25 Oct. 2011, both applications being incorporated herein by reference in their entirety.

FIELD OF THE INVENTION

The present invention relates generally to ultrasonic imaging systems, e.g., for medical imaging, and particularly to methods and systems for suppressing clutter effects in ultrasonic imaging systems.

BACKGROUND OF THE INVENTION

Ultrasonic medical imaging plays a crucial role in modern medicine, gradually becoming more and more important as new developments enter the market. One of the most common ultrasound imaging applications is echocardiography, or ultrasonic imaging of the cardiac system. Other widespread applications are obstetrics and gynecology, as well as abdominal imaging, to name a few. Ultrasonic imaging is also used in various other industries, e.g., for flaw detection during hardware manufacturing.

Ultrasonic imaging systems typically produce relatively noisy images, making the analysis and/or diagnosis of these images a task for highly trained experts. One of the most problematic imaging artifacts is clutter, i.e., undesired information that appears in the imaging plane, obstructing data of interest.

One of the main origins of clutter in ultrasonic imaging is effective imaging of objects outside the probe's mainlobe, also referred to as sidelobe clutter. For example, in echocardiography, the dominant reflectors outside the probe's mainlobe are typically the ribcage and the lungs.

Another origin of clutter is multi-path reflections, also called reverberations. In some cases, the geometry of the scanned tissue with respect to the probe, as well as the local reflective characteristics of the tissue, causes a noticeable percentage of the transmitted energy to bounce back and forth in the tissue before reaching the probe. As a result, the signal measured for a specific range with respect to the probe may include contributions from other ranges, in addition to the desired range. If the signal emanating from other ranges is caused by highly reflective elements, it may have a significant effect on the image quality.

A common method for enhancing the visibility of the desired ultrasonic image relative to the clutter, particularly in patients with low echogenicity (a common phenomenon among obese patients), is administering contrast agents. Such agents enhance the ultrasonic backscatter from blood and aid in its differentiation from the surrounding tissue. This method is described, for example, by Krishna et al., in a paper entitled "Sub-harmonic Generation from Ultrasonic Contrast Agents," Physics in Medicine and Biology, vol. 44, 1999, pages 681-694, which is incorporated herein by reference.

Using harmonic imaging instead of fundamental imaging, i.e., transmitting ultrasonic signals at a certain frequency and receiving at twice the transmitted frequency, also reduces clutter effects. Spencer et al. describe this method in a paper entitled "Use of Harmonic Imaging without Echocardiographic Contrast to Improve Two-Dimensional Image Quality," American Journal of Cardiology, vol. 82, 1998, pages 794-799, which is incorporated herein by reference.

U.S. Pat. No. 6,251,074, by Averkiou et al., issued on Jun. 26, 2001, titled "Ultrasonic Tissue Harmonic Imaging," describes an ultrasonic diagnostic imaging system and methods, which produce tissue harmonic ultrasonic images from harmonic echo components of a transmitted fundamental frequency. Fundamental frequency waves are transmitted by an array transducer to focus at a focal depth. As the transmitted waves penetrated the body, the harmonic effect develops as the wave components begin to focus. The harmonic response from the tissue is detected and displayed, while clutter from fundamental response is reduced by excluding fundamental frequencies.

Furthermore, image-processing methods have been developed for detecting clutter-affected pixels in echocardiographic images by means of post-processing. Zwirn and Akselrod present such a method in a paper entitled "Stationary Clutter Rejection in Echocardiography," Ultrasound in Medicine and Biology, vol. 32, 2006, pages 43-52, which is incorporated herein by reference.

Other methods utilize auxiliary receive ultrasound beams. In U.S. Pat. No. 8,045,777, issued on 25th Oct. 2011, titled "Clutter Suppression in Ultrasonic Imaging Systems," Zwirn describes a method for ultrasonic imaging, comprising: transmitting an ultrasonic radiation towards a target; receiving reflections of the ultrasonic radiation from a region of the target in a main reflected signal and one or more auxiliary reflected signals, wherein each one of the reflected signals is associated with a different and distinct beam pattern, wherein all of the reflected signals have an identical frequency; determining a de-correlation time of at least one of: the main reflected signal and the one or more auxiliary reflected signals; applying a linear combination to the main reflected signal and the one or more auxiliary reflected signals, to yield an output signal with reduced clutter, wherein the linear combination comprises a plurality of complex number weights that are being determined for each angle and for each range within the target tissue, wherein each complex number weight is selected such that each estimated reflection due to the clutter is nullified, wherein a reflection is determined as associated with clutter if the determined de-correlation time is above a specified threshold.

U.S. patent application 2009/0141957, by Yen and Seo, published on Jun. 4, 2009, titled "Sidelobe Suppression in Ultrasound Imaging using Dual Apodization with Cross-Correlation," describes a method of suppressing sidelobes in an ultrasound image, the method comprising: transmitting a focused ultrasound beam through a sub-aperture into a target and collecting resulting echoes; in receive, using a first apodization function to create a first dataset; in receive, using a second apodization function to create a second dataset; combining the two datasets to create combined RF data; calculating a normalized cross-correlation for each pixel; performing a thresholding operation on each correlation value; and multiplying the resulting cross-correlation matrix by the combined RF data.

An additional class of currently available methods for handling clutter is a family of clutter rejection algorithms, used in color-Doppler flow imaging. These methods estimate the flow velocity inside cardiac chambers or other blood vessels and suppress the effect of slow-moving objects; assuming that the blood flow velocity is significantly higher than the motion velocity of the surrounding tissue. These methods are described, for example, by Herment et al. in a paper entitled "Improved Estimation of Low Velocities in Color Doppler Imaging by Adapting the Mean Frequency Estimator to the Clutter Rejection Filter," IEEE Transactions on Biomedical Engineering, vol. 43, 1996, pages 919-927, which is incorporated herein by reference.

SUMMARY OF THE INVENTION

Embodiments of the present invention provide methods and devices for reducing clutter effects in ultrasonic imaging systems.

The present invention provides a method of ultrasound imaging, said method comprising: transmitting ultrasound radiation towards a target and receiving reflections of the ultrasound radiation from a region of the target in a main reflected signal and one or more auxiliary reflected signals, wherein each one of the reflected signals comprises an input dataset and is associated with a beam with a different and distinct beam pattern; compounding the input datasets from the main reflected signal and one or more auxiliary reflected signals, by the use of a compounding function, said compounding function using parameters derived from spatial analysis of the input datasets, said compounding function parameters being derived from at least one of:
(a) The local phase difference and/or magnitude difference and/or magnitude ratio and/or complex signal ratio between different receive beams, and/or functions of one or more of the aforementioned parameters;
(b) Spatial functions of the local phase difference and/or magnitude difference and/or magnitude ratio and/or complex signal ratio between different beams;
(c) The local difference and/or ratio between spatial functions of the local magnitude and/or phase and/or complex signal in the different receive beams;
(d) Applying multiple temporal band-pass filters to the local magnitude and/or phase and/or complex signal in the different receive beams, applying spatial analysis to the outputs of multiple temporal band-pass filters and compounding the results;
(e) Applying multiple temporal band-pass filters to the local phase difference and/or magnitude difference and/or magnitude ratio and/or complex signal ratio between different receive beams, applying spatial analysis to the outputs of multiple temporal band-pass filters and compounding the results; or
(f) Spatial-temporal functions of the local phase difference and/or magnitude difference and/or magnitude ratio between different beams, wherein spatial derivatives of the local phase difference and/or magnitude difference and/or magnitude ratio between different beams, are applied after local temporal filtering; or wherein the local difference and/or ratio between spatial functions of the magnitude and/or phase and/or complex signal in the different beams are applied after local temporal filtering.
Other aspects of the present invention are detailed in the claims.

BRIEF DESCRIPTION OF THE DRAWINGS

The invention for clutter suppression in ultrasonic imaging systems is herein described, by way of example only, with reference to the accompanying drawings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION OF EMBODIMENTS

System Description

Figure 1A:
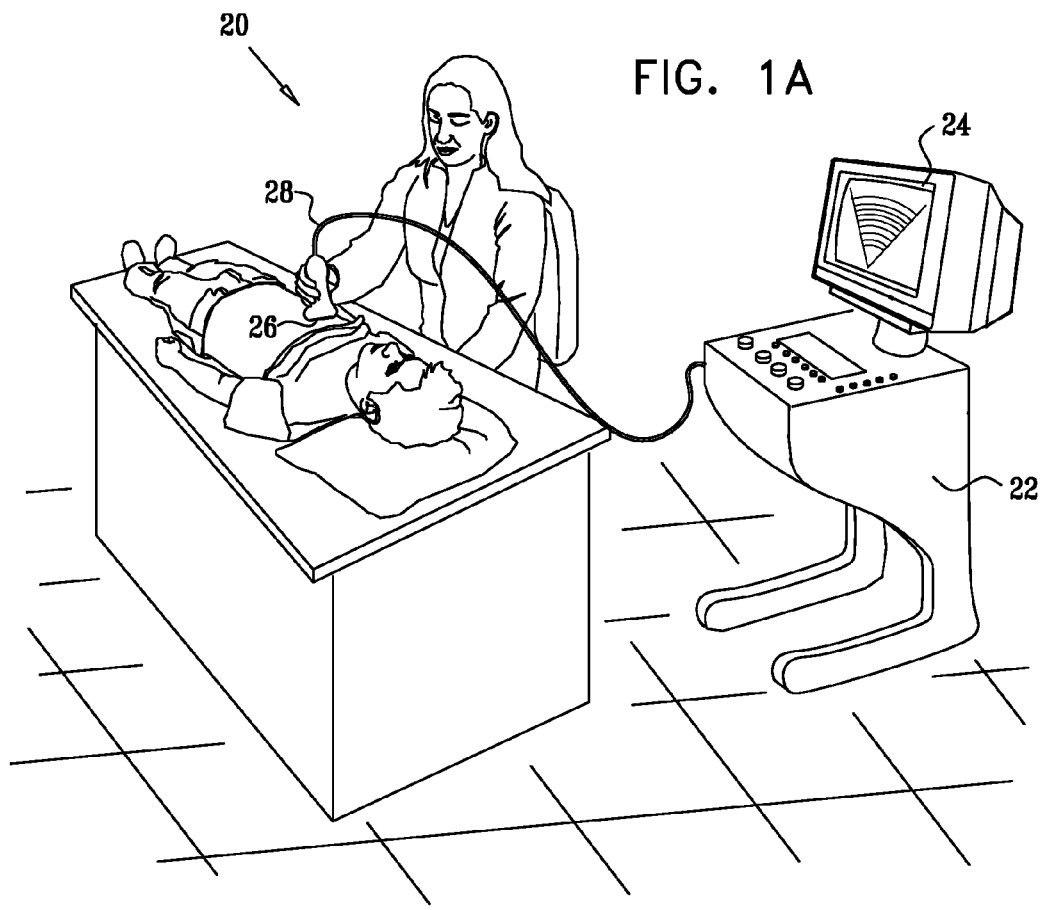
FIG. 1A is a schematic, pictorial illustration of an ultrasonic imaging system, in accordance with an embodiment of the present invention.

In broad terms, the present invention relates to methods and systems for suppressing clutter effects in ultrasonic imaging systems. In some embodiments, these methods and systems also result in enhancement of the ultrasound images' lateral resolution, i.e., the resolution along directions perpendicular to the centerline of an ultrasound beam.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

FIG. 1A is a schematic, pictorial illustration of an ultrasonic imaging system 20, in accordance with an embodiment of the present invention.

System 20 comprises an ultrasound scanner 22 that scans organs of a patient using ultrasound radiation. A display unit 24 displays the scanned images. A probe 26, connected to scanner 22 by a cable 28, is typically held against the patient body in order to image a particular body structure, such as the heart (referred to as a "target"). Alternatively, the probe may be adapted for insertion into the body, e.g., in transesophageal or transvaginal configurations. The probe transmits and receives ultrasound beams required for imaging. Scanner 22 comprises control and processing circuits for controlling probe 26 and processing the signals received by the probe.

Figure 1B:
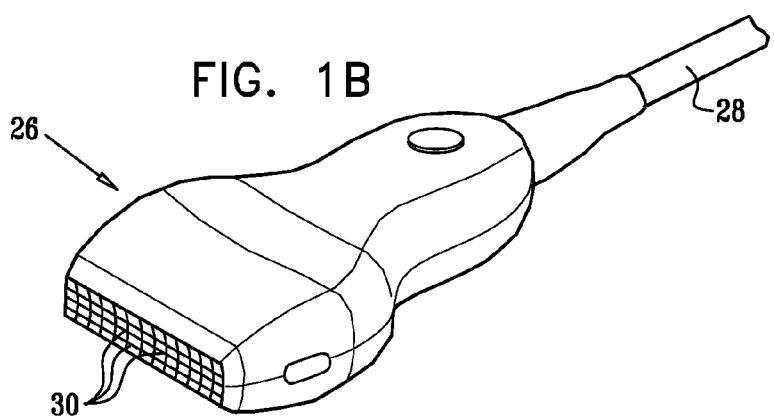
FIG. 1B is a schematic, pictorial illustration of a probe used in an ultrasonic imaging system, in accordance with an embodiment of the present invention.

FIG. 1B is a schematic, pictorial illustration of probe 26 used in imaging system 20, in accordance with an embodiment of the present invention. The probe comprises an array of transducers 30, e.g., piezoelectric transducers, which are configured to operate as a phased array. On transmission, the transducers convert electrical signals produced by scanner 22 into a beam of ultrasound radiation transmitted into the patient's body. On reception, the transducers receive the ultrasound radiation reflected from different body tissues, and convert it into electrical signals sent to scanner 22 for processing.

Probe 26 typically comprises several dozens and up to several hundreds of transducers 30 arranged in a horizontal linear array. The horizontal aperture of the array, typically of the order of several centimeters, affects the minimal horizontal beam-width of the probe and the resulting horizontal angular resolution. The vertical beam-width may be adjusted by an acoustic lens. Some probes, referred to as "1½ dimensional probes," comprise several rows of transducers in the vertical dimension, providing a vertical sector-like beam pattern. Other probes comprise a complete two-dimensional (or multi-dimensional) array of transducers, enabling control over both horizontal and vertical directional beam patterns. The terms "horizontal" and "vertical" are used here solely for convenience, as the array may be positioned during imaging in any appropriate orientation relative to the patient's body.

A single array of transducers may generate different beam patterns, whose mainlobe may be pointed at different directions. On transmission, the direction of the mainlobe is typically set by adjusting the relative phase and/or the relative time delay of the signals fed to the different transducers. On reception, the direction of the mainlobe is usually set by adjusting the phase shift and/or time delay introduced to the signal received by each transducer.

The beam pattern on both transmission and reception may be adjusted by applying different apodizations. On reception, apodization is a process of multiplying the output signal of each transducer by a multiplicative coefficient ("apodization coefficient"), before combining the outputs of all transducers to generate an overall array output signal. A reciprocal process is performed on transmission (in many cases a constant apodization is used on transmission).

Let k be the transducer index (k should go over all transducers even if the transducer array comprises of more than one dimension), $s_k$ be the signal measured by transducer k, $a_k$ be the apodization coefficient of transducer k on reception, and $\phi_k$ be the phase shift for transducer k on reception. Beamforming on reception, for obtaining the signal S at time t, may be performed using eq. (1):

$$S(t)=\Sigma_k a_k(t)e^{j\phi_k(t)}s_k(t) \quad (1)$$

Alternatively, when using time-delays instead of phase shifts, where $\tau_k$ is the time-delay for transducer k, one may use eq. (2) for beamforming on receive:

$$S(t)=\Sigma_k a_k(t)s_k(t-\tau_k) \quad (2)$$

Similar equations may be used for combined time-delay and phase-shift design. Comparable equations may also be utilized on transmission.

Depending on system design, the signal reaching the different transducers may be sampled (by one or more analog-to-digital converters in scanner 22) at different beamforming stages, e.g., for each transducer separately, for different groups of transducers, or for all transducers combined. Eq. (1) and eq. (2) and combinations or variations thereof are applicable to all these cases.

Moreover, some systems perform sampling for all transducers combined (i.e., at the beam level), but use more than one set of apodization coefficients $a_k$ and/or more than one set of phase shifts $\phi_k$ and/or more than one set of time-delays $\tau_k$, a setting commonly referred to as multi-line acquisition, or MLA. In MLA configurations, the beam pattern used on transmission is typically wider than those used on reception, so as to provide ultrasound energy to most or all of the volume covered by the different receive beams.

Certain scanners 22 apply filtering matched to the transmitted waveform and/or down-conversion analogically, before sampling, whereas others apply matched filtering and/or down-conversion digitally. The matched filtering and/or down-conversion may be applied in any of the beamforming stages.

Some scanners 22 sample the real data at one or more of the beamforming stages, whereas others use quadrature receivers, providing complex samples, including both a real in-phase component and an imaginary quadrature component.

Further types of scanners 22 use multiple concurrent beams on transmission, each of which having a different waveform (e.g., different central transmission frequency, different pulse encoding configuration). In these cases, each receive beam is typically generated using a specific matched filter, corresponding to one of the transmission waveforms.

Note that in some probe designs, a planar array is used instead of a phased array. In such cases, only a small set of predefined time-delays and/or phase-shifts is supported by the transducer array, wherein the beam formed by each such set is typically sampled separately. Further probe designs do not use transducer arrays, but instead allocate a single transducer to each transmit and/or receive beam.

Probe 26 typically scans the region of interest, which may be one-dimensional (1D), two-dimensional (2D) or three-dimensional (3D), by one or more of the following:

(a) Electronic beam-steering, i.e., changing the direction of the mainlobe by adjusting the relative phase and/or the relative time delay of the signals fed to the different transducers.

(b) Electronic change of the phase center of the transducer array, performed by adjusting the apodization pattern, e.g., by setting certain regions of the apodization pattern to 0. As a result, the vector between the phase center of the beam and the peak of its mainlobe (the "beam direction") may be spatially shifted, producing another vector parallel to the former one.

(c) Mechanical beam-steering, i.e., mechanically moving portions of or all of the transducer array, thus affecting the direction of its mainlobe.

System Configurations for Clutter Suppression

In embodiments of the present invention, one or more auxiliary receive beams are used for suppressing clutter effects. The auxiliary receive beams may be generated using any configuration known in the art, including but not limited to those described hereinabove.

Auxiliary receive beams may be allocated separately for each beam used normally for imaging ("main beam"), or for groups of main beams. The latter configuration may be useful, e.g., in MLA configurations, where multiple main beams are typically used concurrently on reception, corresponding to a single transmission beam, and one or more auxiliary beams may be defined.

The auxiliary receive beams may be generated at the same time as the corresponding main receive beam or beams, or at different times. Combinations can also be considered, i.e., some of the auxiliary receive beams may be generated at the same time as the corresponding main receive beam or beams, and others may be generated at different times. Various sequences of relative timing between the different beams may be defined, e.g., alternating generation of main and auxiliary receive beams. If some or all of the auxiliary receive beams are generated at different times than the corresponding main receive beam or beams, separate transmission beams may be used for the main and auxiliary receive beams or groups thereof, using the same or different beam patterns.

In exemplary embodiments, one main receive beam and one auxiliary receive beam are utilized, corresponding to a single transmission beam or two separate transmission beams. In such a case, the auxiliary receive beam may have a different beam pattern than the main receive beam, e.g., it may be pointed at the same direction but its beam width may be wider (or narrower).

In further exemplary embodiments, corresponding to an MLA configuration, multiple concurrent main receive beams (e.g., 16 or 32) may be used with a single transmission beam, and one auxiliary receive beam is added, to be used for all concurrent receive beams. In most MLA cases, the beam patterns for all main receive beams are similar, but each main receive beam points at a slightly different direction. In order to provide reference information for all main receive beams, the auxiliary receive beam may be wider than some of them, e.g., its width may match that of the transmission beam.

In even further exemplary embodiments, multiple main receive beams may be used with a single transmission beam, wherein one or more auxiliary receive beams may be added for each main receive beam or for each group of main receive beams.

In certain embodiments, one or more receive beams may be treated as both main receive beams and auxiliary receive beams, in the context of different computations.

Clutter Suppression Method

In the embodiments of the present invention, compound information is provided by one or more main receive beams and one or more auxiliary receive beams so as to provide clutter suppressed outputs. The process may be applied in various processing phases of scanner 22, and to different types of data, e.g., analogically or digitally, to real or complex samples, before or after matched filtering and/or down-sampling.

In some cases, conversions which would be easily understood by people knowledgeable in the art may be required. For example, some embodiments require that the input data for each receive beam would be complex. In such cases, if the input data for one or more receive beams is real, a Hilbert transform may be applied to the real data for each receive beam, and an inverse Hilbert transform may be applied to the clutter suppression outputs if necessary.

In configurations where scanner 22 performs sampling for each transducer separately or for different groups of transducers, the clutter suppression process may be applied separately for different groups of transducers. In such cases, "synthetic" main and auxiliary receive beams may be defined for computation purposes only, for each group of transducers separately, and the clutter suppressed outputs for the different transducer groups may be used for further stages of beamforming.

In certain embodiments, the information for each main receive beam and/or auxiliary receive beam may be described as an array of real or complex measurements, each of which corresponding to a certain volume covered by the mainlobe (and sidelobes) of the applicable beam, between consecutive iso-time surfaces of the ultrasound wave within the medium (with respect to the probe 26), typically but not necessarily matching constant time intervals. Each such volume is commonly referred to as a volume pixel, or voxel. The samples are commonly referred to as range-gates, since the speed of sound does not change significantly while traversing soft tissues, so that iso-time surfaces can approximately be referred to as iso-range surfaces.

In some embodiments, a 1D, 2D or 3D region of interest is scanned by scanner 22. The scanning may be performed by any method known in the art, including but not limited to the techniques mentioned hereinabove. For example, different beams may have the same phase center but different beam directions. In such cases, a polar coordinate system is typically used in 2D scanning, and a spherical coordinate system is typically used in 3D scanning. When using a polar coordinate system, the location of each voxel may be defined by the corresponding range-gate index and the angular direction of the beam with respect to the broadside of probe 26, wherein the probe's broadside is defined by a line perpendicular to the surface of probe 26 at its phase center, and wherein said angular direction may be defined in a Euclidian space by an azimuth angle, or by the u coordinate in sine-space. Similarly, when using a spherical coordinate system, the location of each voxel may be defined by the corresponding range-gate index and the angular direction of the beam with respect to the broadside of probe 26, wherein the angle direction may be defined either by the azimuth and elevation angles and/or by the (u,v) coordinates in sine-space.

Additionally or alternatively, different beams may have different phase centers, wherein the beams may or may not be parallel to each other. In the case of parallel beams, a 2D or 3D Cartesian coordinate system may be used, wherein the location of each voxel is defined by its corresponding range-gate index and the location of the phase center.

Regardless of the scanning method and coordinate system used, the dataset collected by one or more receive beams, which may or may not be concurrent, in each time-swath ("frame") may be organized in a 1D, 2D or 3D array ("scanned data array"), using any voxel arrangement known in the art, wherein each index into the arrays relates to a different axis (e.g., in a polar coordinate system, a range-gate index and an azimuth index may be utilized), so that voxels which are adjacent to each other in one or more axes of the coordinate system also have similar indices in the corresponding axes. In certain cases, the scanned data array may use a coordinate system which does not correspond to the scanning method, e.g., all receive beams may have the same phase center but different beam directions, but the scanned data array may utilize Cartesian rather than polar or spherical coordinates. This may be obtained by spatial interpolation and/or extrapolation, using any method known in the art, e.g., nearest neighbor interpolation, linear interpolation, spline or smoothing spline interpolation, and so forth.

In some embodiments, the scanned data array adheres to the following requirements, in which case the scanned data arrays are referred to as "common configuration scanned data arrays":

(a) All the data in a scanned data array corresponds to receive beams with the same beam pattern, except, perhaps, for translations and/or rotations.

(b) All the data in a scanned data array corresponds to receive beams using the same central frequency on reception.

(c) All the data in the scanned data array corresponds to receive beams used in conjunction with transmit beams using the same waveforms and the same transmit beam pattern, except, perhaps, for translations and/or rotations.

(d) The data in a scanned data array originates from receive beams which may be concurrent, divided into multiple groups each of which is concurrent (this is the most common case when using MLA configurations), or non-concurrent. In other embodiments, one or more of requirements (a)-(d) may not be met.

Compounding Functions

In exemplary embodiments, the compounding of information provided by a main receive beam and one or more associated auxiliary receive beams is performed by computing a function of the local signal in two or more receive beams ("compounding function"), wherein the term local signal refers to a certain volume region, which is partially or wholly covered by more than one of the receive beams, e.g., a certain range-gate index of the different receive beams in cases where multiple receive beams have the same sampling frequency. The local signal in each such receive beam may be generated by setting the matched filters to fundamental imaging, i.e., using a reception frequency band centered at the center frequency of the corresponding transmission beam, or to harmonic imaging, i.e., using a reception frequency band centered at a frequency which is a natural number multiplied by the center frequency of the corresponding transmission beam (harmonies of the transmission frequencies). In some embodiments, different receive beams may use different harmonies of the transmission frequencies, including but not limited to first harmonies (i.e., fundamental imaging). The output of the compounding function for each entry into the scanned data array and/or each frame may be used instead of the measured signal for the main receive beam in any further processing performed by ultrasound imaging systems, such as:

(a) Log-compression, i.e., computing the logarithm of the local signal magnitude.
(b) Time-gain control, i.e., applying a range-dependent correction for the signal attenuation within the medium.
(c) Global gain control.
(d) Doppler processing, e.g., for color-Doppler flow imaging, tissue-Doppler imaging, and/or pulse-Doppler studies. Note that Doppler processing typically entails analyzing data from two or more pulses for each applicable voxel.

In some embodiments, the compounding function may use parameters ("compounding function parameters") derived from at least one of:

(a) The local phase difference and/or magnitude difference and/or magnitude ratio between different receive beams, and/or functions of one or more of the aforementioned parameters, e.g., the magnitude ratio converted into decibel units.
(b) Spatial functions of the local phase difference and/or magnitude difference and/or magnitude ratio between different beams, e.g., various spatial derivatives of said parameters, using any operator known in the art, such as $$\frac{1}{3}\begin{pmatrix} -1 & 0 & 1 \\ -1 & 0 & 1 \\ -1 & 0 & 1 \end{pmatrix} \text{ and } \frac{1}{3}\begin{pmatrix} -1 & -1 & -1 \\ 0 & 0 & 0 \\ 1 & 1 & 1 \end{pmatrix}.$$

(c) The local difference and/or ratio between spatial functions of the local magnitude and/or phase and/or complex signal in the different receive beams, e.g., the ratio of local magnitude derivatives along a certain spatial axis; the ratio of local normalized magnitude derivatives along a certain spatial axis, wherein a local normalized derivative is defined as the local signal derivative divided by the local signal; the ratio of local magnitude spatial derivatives, wherein the spatial derivative is computed using a "Laplacian filter", i.e., $$\frac{1}{8}\begin{pmatrix} -1 & -1 & -1 \\ -1 & 8 & -1 \\ -1 & -1 & -1 \end{pmatrix};$$

the ratio of local magnitude normalized spatial derivatives, wherein the spatial derivative is computed using a "Laplacian filter"; the ratio of normalized magnitude spans, wherein a normalized signal span is defined as the difference between the maximal and minimal value, divided by the mean value, wherein an outlier rejection scheme may be applied prior to the statistical functions minimum, maximum and/or mean; and so forth.

(d) Temporal functions of the local phase difference and/or magnitude difference and/or magnitude ratio between different beams, e.g., various temporal low-pass, band-pass or high-pass filters.
(e) Spatial-temporal functions of the local phase difference and/or magnitude difference and/or magnitude ratio between different beams, e.g., spatial derivatives of the local phase difference and/or magnitude difference and/or magnitude ratio between different beams, applied after local temporal filtering; local difference and/or ratio between spatial functions of the magnitude and/or phase and/or complex signal in the different beams, applied after local temporal filtering; and so forth.

In that context, spatial filtering may be applied to the scanned data array for a specific frame, whereas the temporal filtering may be applied to a specific voxel or group of adjacent voxels over multiple consecutive frames.

In some embodiments, one or more of the following assumptions may be utilized when selecting and/or making use of the compounding function parameters:

(a) The local phase difference and/or magnitude difference and/or magnitude ratio are indicative of the angular direction of the signal source. By definition, non-clutter signals originate from angular directions close to that of the mainlobe of a main receive beam. For example, when using a main receive beam and an auxiliary receive, whose mainlobes point at the same spatial angle, one would expect that for reflectors at the center of the mainlobes, which by definition generate non-clutter signals:

(i) the local phase difference between the main and auxiliary receive beams would be close to 0;
(ii) the local magnitude ratio between the main and auxiliary receive beams, wherein the auxiliary receive beam's signal is normalized so that its maximal gain matches the maximal gain of the main receive beam, would be close to 1.0; and
(iii) the local magnitude difference between the main and auxiliary receive beams, wherein the auxiliary receive beam's signal is normalized so that its maximal gain matches the maximal gain of the main receive beam, would be close to 0.0.

Figure 2:
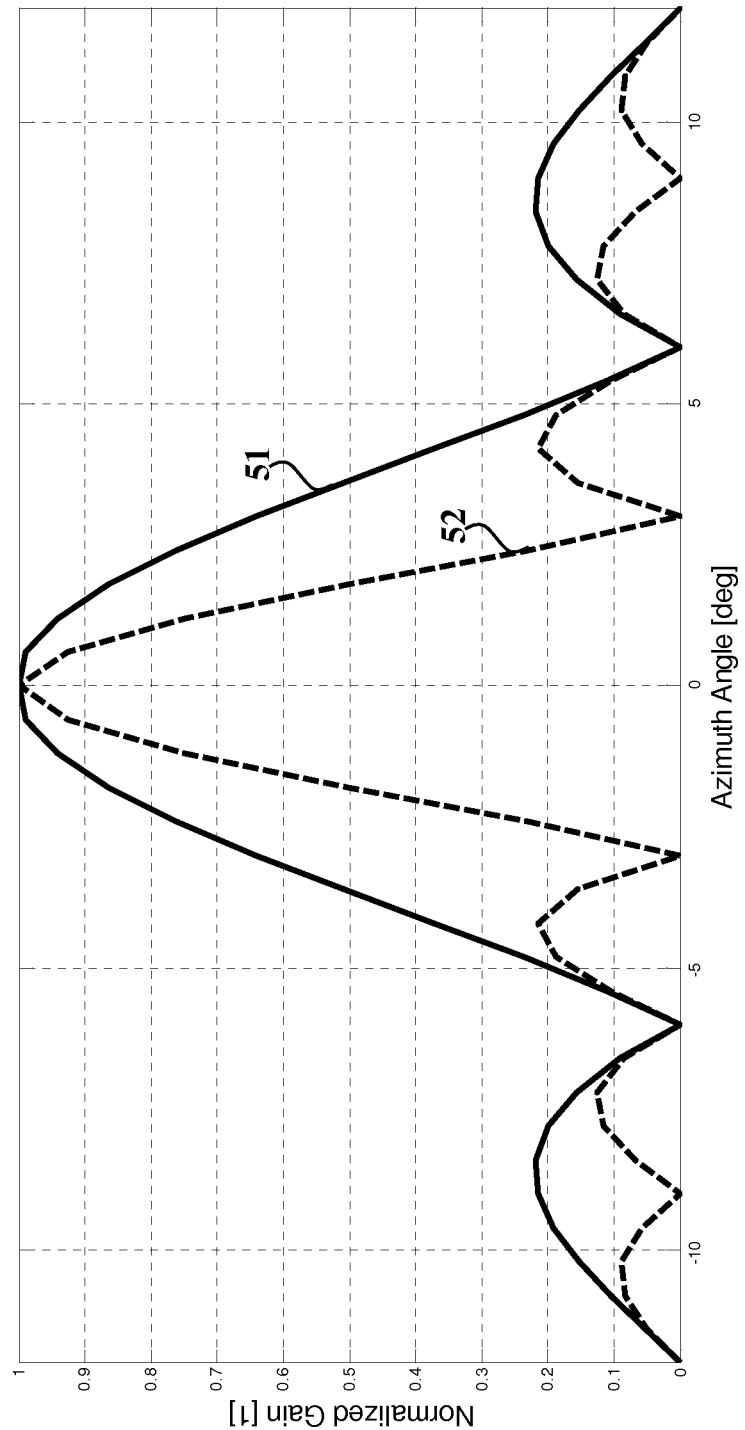
FIG. 2 is a schematic illustration of the beam pattern of two exemplary receive beams, defined in terms of gain as a function of the azimuth angle, in accordance with an embodiment of the present invention.
Figure 3A:
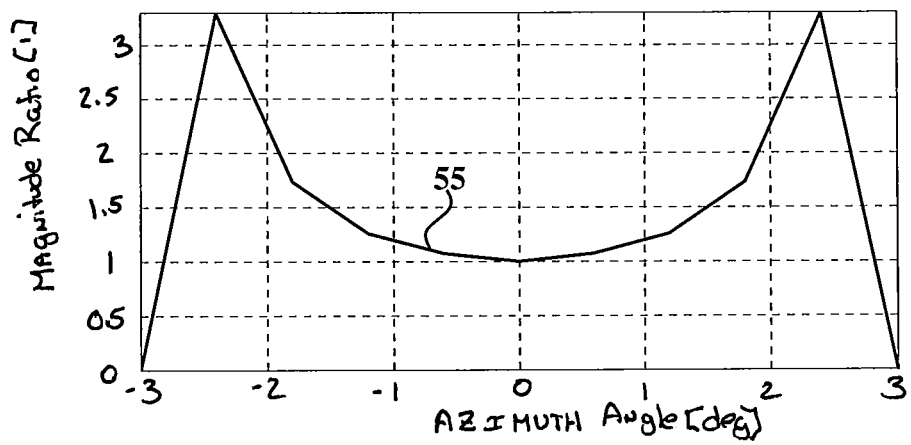
FIG. 3A is a schematic illustration of the expected magnitude ratio between the two receive beams of FIG. 2, defined for a point-like reflector as a function of the azimuth angle, wherein the azimuth scale is different than that in FIG. 2, providing a zoom on angles close to 0°, in accordance with an embodiment of the present invention.
Figure 3B:
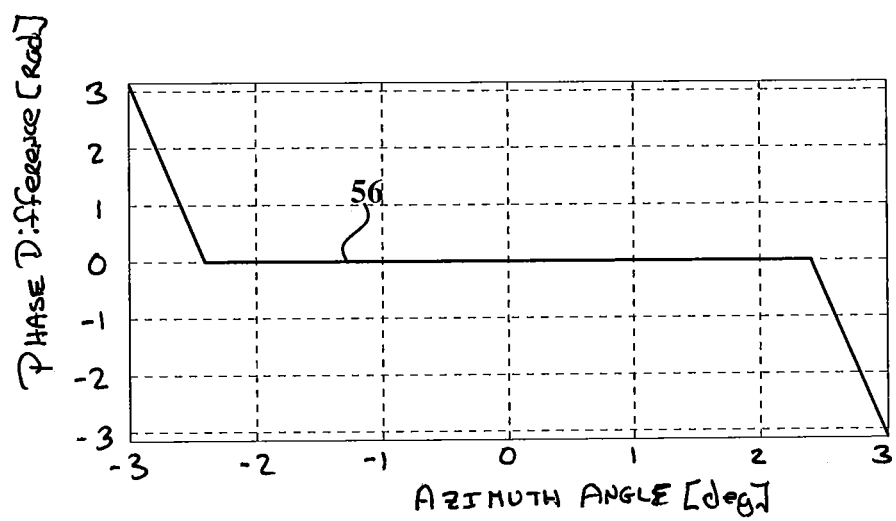
FIG. 3B is a schematic illustration of the expected phase difference between the two receive beams of FIG. 2, defined for a point-like reflector as a function of the azimuth angle, wherein the azimuth scale matches that of FIG. 3A, in accordance with an embodiment of the present invention.

These assumptions may be derived from beamforming equations such as eq. (1) and eq. (2). A schematic illustration of two exemplary beam patterns, 51 and 52, defined in terms of gain as a function of the azimuth angle, is shown in FIG. 2. The resulting magnitude ratio between the main and auxiliary receive beams, defined for a point-like reflector as a function of the azimuth angle, can be seen in graph 55 in FIG. 3A. The resulting phase difference between the main and auxiliary receive beams, defined for a point-like reflector as a function of the azimuth angle, can be seen in graph 56 in FIG. 3B. Note that the azimuth angle scale in FIG. 3B matches that of FIG. 3A, but does not match that of FIG. 2.

Similarly, when using a main receive beam and an auxiliary receive, whose mainlobes do not point at the same spatial angle, one would expect that for reflectors at the center of the mainlobes, which by definition generate non-clutter signals:
(i) the local phase difference between the main and auxiliary receive beams would be close to a constant, which may be calculated based on the spatial angles of the mainlobes of the main and auxiliary receive beams; and
(ii) the local magnitude ratio between the main and auxiliary receive beams, wherein the auxiliary receive beam's signal is normalized so that its maximal gain matches the maximal gain of the main receive beam, would be close to a constant, which may be calculated based on the spatial angles of the mainlobes of the main and auxiliary receive beams.

It should be noted that any local phase difference and/or magnitude difference and/or magnitude ratio may correspond to more than one angular direction of the signal source. For example, when using a main receive beam and an auxiliary receive beam, whose mainlobes point at the same spatial angle, wherein both the main receive beam and the auxiliary receive beam have a beam pattern which is symmetric about the center of their mainlobes (e.g., a conical beam pattern), at any given range with respect to the phase center of the transducer array, one would expect the local phase difference and magnitude difference and magnitude ratio to be equal along concentric circular curves, whose center falls at the centerline of the mainlobes, wherein the curves lie in the corresponding range with respect to the phase center of the transducer array. Some deviations from this rule may be caused by physical effects within the medium, such as diffraction, which affect the actual beam pattern within the scanned region.

By using more than one of the following parameters: the local phase difference, the local magnitude difference, and the local magnitude ratio, one may reduce the ambiguity in the information regarding the angular direction of the signal source. By utilizing information from multiple auxiliary receive beams for a given main receive beam, said ambiguity may be further reduced.
(b) For non-clutter signals, which originate from angular directions approximately corresponding by definition to the center of the main receive beam's mainlobe, one would expect the signal level and/or its magnitude as a function of spatial location, to change in a similar fashion in the main and auxiliary receive beams, assuming that the mainlobes of the main and auxiliary receive beams sufficiently overlap, and that the data for the auxiliary beams is normalized so that the auxiliary beam's maximal gain would match the maximal gain of the corresponding main beam. In that context, the signal level as a function of spatial location may be defined, for example, by the local signal level, the local spatial derivatives and/or the local normalized spatial derivatives, wherein a local normalized spatial derivative is defined as the local spatial derivative divided by the local signal.

It should be noted that the lateral resolution of various receive beams may be different due to differences in the corresponding beam patterns, and that the axial resolution of various receive beams may be different due to dissimilar waveforms on transmission and/or reception. Therefore, in some embodiments, before comparing the signal level and/or its magnitude as a function of spatial location between different receive beams, spatial filtering may be applied to one or more datasets, each of which corresponding to a specific type of beam pattern and/or waveform, in order to make sure that the lateral and/or axial resolution of the local signal in the compared beams would match. When using multiple common configuration scanned data arrays, each of which corresponding to receive beams with specific lateral and/or axial resolutions, spatial filtering may be applied to one or more of the common configuration scanned data arrays before comparing the signal level and/or its magnitude as a function of spatial location between different receive beams. For example, when using narrow main receive beams and wide auxiliary receive beams, wherein for each main receive beam there is a corresponding auxiliary beam whose mainlobe points at the same direction, one may apply a spatial low-pass filter to the common configuration scanned data arrays acquired with the main receive beam.

(c) Different target regions may have different dynamic models. For example, in echocardiography, the ribcage, which often causes clutter reflections, moves at much slower rates than the heart muscle within the region of interest. Various temporal filters may be employed in order to estimate the signal levels for tissues with predefined dynamic properties. The clutter suppression processes described herein may be applied to specific frequency bands. Additionally or alternatively, one may apply the clutter suppression processes described herein separately to outputs of several temporal filters, and then compound the results in order to obtain the final dataset.

The compounding function parameters may be derived and/or utilized in one or more of the following manners ("compounding function implementation manners"):
(a) Computed for each entry into the scanned data array and each frame separately, and applied accordingly.
(b) Computed for a predefined subset of the frames, and in each frame—for each entry into the scanned data array or group of adjacent entries, and applied to all frames, wherein the parameters applied in a specific frame may be the ones computed for the closest frame index, or alternatively, the closest frame index which is equal to or lower than the current frame index. Spatial interpolation and/or interpolation in time may also be used in order to derive the parameters applied in a given frame.
(c) Computed for a specific frame but for each entry into the scanned data array or group of adjacent entries, and applied to all frames.
(d) Computed for all frames but for a specific set of entries into the scanned data array, and applied to all entries into the scanned data array, wherein in each frame, the parameter value for each voxel is derived by interpolation and/or extrapolation, e.g., using nearest neighbor interpolation.
(e) Computed for a predefined subset of the frames, whose length may also equal 1, and for a specific set of entries into the scanned data array, wherein in each frame, the parameter values are based on those computed for the closest frame index, on those computed for the closest frame index which is equal to or lower than the current frame index, or on interpolation and/or extrapolation in time, and wherein spatial interpolation and/or extrapolation is used for each entry into the scanned data array. The interpolation and/or extrapolation may utilize any method known in the art.

Methods (b)-(e) are designed to reduce the time and/or memory complexity of the computations.

Generalized Metrics

In certain embodiments, one or more of the compounding function parameters may be defined as adhering to at least one of the following options:

(a) Indicative of the probability for the corresponding voxel to be substantially affected by clutter effects only (i.e., almost all its received energy originates from clutter effects), as derived using certain physical and/or physiologic assumptions.

(b) Indicative of the probability for the corresponding voxel to be substantially unaffected by clutter effects, as derived using certain physical and/or physiologic assumptions. Note that, for each specific voxel, the sum of the probabilities in (a) and (b) is always 1.0.

(c) Indicative of the percentage of the received energy within the corresponding voxel that originates from clutter effects.

(d) Set to a certain constant, e.g., 0.0, if the corresponding voxel is not significantly affected by clutter effects, and otherwise to a different constant, e.g., 1.0.

Such compounding function parameters are referred to herein as "generalized metrics." They may be computed using any method known in the art. In some embodiments, e.g., in option (d), segmentation techniques may applied to at least one of the following (commonly referred to as the "segmentation technique parameters"): (a) the local received signal in one or more of the receive beams; and (b) the local value of one or more of the compounding function parameters.

For instance, classic edge detection (see, for example, U.S. Pat. No. 6,716,175, by Geiser and Wilson, issued on Apr. 6, 2004, and titled "Autonomous boundary detection system for echocardiographic images") or radial search techniques (see, for example, U.S. Pat. No. 5,457,754, by Han et al, issued on Oct. 10, 1995, and title "Method for automatic contour extraction of a cardiac image") may be used for segmentation purposes. Such techniques may be combined with knowledge-based algorithms, aimed at performance enhancement, which may either be introduced during post-processing, or as a cost-function, incorporated with the initial boundary estimation. Another example for an applicable segmentation method is solving a constrained optimization problem, based on active contour models (see, for example, a paper by Mishra et al., entitled "A GA based approach for boundary detection of left ventricle with echocardiographic image sequences," Image and Vision Computing, vol. 21, 2003, pages 967-976, which is incorporated herein by reference). Additionally or alternatively, one may apply a predefined threshold to one or more of the segmentation technique parameters, in order to obtain an initial division between voxels that are significantly affected by clutter effects and voxels that are not. In some embodiments, iterative region growing techniques may then be employed, wherein the predefined threshold for one or more of the segmentation technique parameters may be changed between consecutive iterations.

In further embodiments, the generalized metrics may be defined as real numbers whose values range from 0.0 to 1.0, wherein the value 0.0 is assigned to voxels that are substantially unaffected by clutter effects, and the value 1.0 is assigned to voxels in which substantially all of the measured signal emanates from clutter effects ("normalized generalized metrics"). In options (a)-(b) immediately above, the normalized generalized metrics can be referred to as the estimated probability for the corresponding voxel to be substantially affected by clutter effects only; in option (c) immediately above, the normalized generalized metrics can be referred to as the estimated percentage of the received energy within the corresponding voxel that originates from clutter effects. Such definitions simplify signal calibration, especially when the compounding function is linear. In that context, the term "signal calibration" refers to making sure that the signal energy in voxels completely unaffected by clutter effects changes as little as possible due to the clutter suppression process, whereas the signal energy in voxels whose sole energy source is clutter would be suppressed as much as possible by the clutter suppression process.

In certain embodiments, the generalized metric for a set of voxels in a set of frames may be derived using the following four-step process:

(a) Select one or more compounding function parameters to be used ("compounding function parameter set"). Some examples for compounding function parameter sets:

(i) parameter #1: the local magnitude ratio between two different receive beams (a main and an auxiliary beam);
parameter #2: the local phase difference between two different receive beams;

(ii) parameter #1: the local ratio of spatial magnitude derivatives along a first spatial axis (e.g., the X axis) between two different receive beams;
parameter #2: the local ratio of spatial magnitude derivatives along a second spatial axis (e.g., the Y axis) between two different receive beams;

(iii) parameter #1: the local ratio of normalized spatial magnitude derivatives along a first spatial axis (e.g., the X axis) between two different receive beams;
parameter #2: the local ratio of normalized spatial magnitude derivatives along a second spatial axis (e.g., the Y axis) between two different receive beams;
wherein a normalized local signal derivative is defined as the local signal derivative divided by the local signal;

(iv) parameter #1: the ratio of local magnitude spatial derivatives between two different receive beams, wherein the spatial derivative is computed using a "Laplacian filter";
parameter #2: the local magnitude ratio between two different beams;

(v) parameter #1: the ratio of local normalized magnitude spatial derivatives between two different receive beams, wherein the normalized spatial derivative is computed by dividing the local output of a "Laplacian filter" (applied to the local signal magnitude) by the local signal magnitude;
parameter #2: the local magnitude ratio between two different receive beams; and (vi) parameter #1: the ratio of the normalized magnitude spans between two different receive beams, wherein a normalized magnitude span is defined as the difference between the maximal and minimal magnitudes (with or without outlier rejection) within a local region, divided by the mean magnitude in said region, wherein the local region is defined so that its width is greater than its height;
parameter #2: the ratio of the normalized magnitude spans between two different beams, wherein the local region is defined so that its height is greater than its width.

(b) Define a model for at least one of:

(i) the probability (or a simple function thereof, such as the probability density function) for a voxel to be substantially affected by clutter effects only;

(ii) the probability (or a simple function thereof, such as the probability density function) for a voxel to be substantially unaffected by clutter effects; and (iii) the percentage of the energy within the corresponding voxel that originates from clutter effects (or a simple function thereof);

as a function of the compounding function parameter set values or the values for a subset of the compounding function parameter set ("compounding model"). In some cases, more than one compounding model may be employed, using one or more subsets of the compounding function parameter set ("compounding function parameter subsets"). In that context, the term "subset" also includes the option of the entire set.

(c) Compute the compounding function parameter set for each relevant voxel and/or its immediate vicinity. In that context, the immediate vicinity may be defined in space and/or in time over the scanned data array.

(d) For each relevant voxel, use the one or more compounding models to estimate at least one of the following (or a simple function thereof):

(i) the probability for its being substantially affected by clutter effects only;

(ii) the probability for its being substantially unaffected by clutter effects; and (iii) the percentage of the energy within the corresponding voxel that originates from clutter effects.

For each compounding model, the results for each relevant voxel may be used as a generalized metric or a normalized generalized metric for that voxel. Multiple generalized metrics may thus be defined for each voxel.

The compounding model may be defined using any method known in the art. Additionally or alternatively, it may be defined in one of more of the following ways:

(a) A predefined model ("predefined compounding model"), which may be theoretically determined and/or experimentally derived. Such a model may be based on the beam pattern of applicable transmit and/or receive beams. For example, the beam width in one or more axes of each such beam may be taken into account. It may be independent of spatial location and time, but it may also be dependent on spatial location and/or time. For example, one may use the fact that in the far-field, the nominal transmit beam width changes as a function of the distance from the probe, reaching a minimum at the focal length. Another example would be to use different models for different beam patterns, if more than one beam pattern type is in use.

(b) A simplified adaptive model ("simplified adaptive compounding model"), based on an assumption regarding the shape of the probability density function (PDF) for a voxel to be substantially affected (or substantially unaffected) by clutter effects as a function of the applicable compounding function parameter subset ("compounding model PDF"). For example, a one-dimensional or multi-dimensional Gaussian function may be used, wherein the function's dimensions should correspond to the number of parameters in the compounding function parameter subset.

The free parameters (in the example of the Gaussian function—the vector of expectation values and the covariance matrix) may be determined by statistical analysis of the values of the compounding function parameter set over some or all of the relevant voxels in the appropriate receive beams. In some embodiments, all relevant voxels in all frames may be used at once. In other embodiments, the computations may be performed separately for each frame and/or each group of voxels. In that context, groups of voxels may be separated in one or more of the scanned data array axes (e.g., different range swaths and/or different angular sections with respect to the broadside of the probe). In further embodiments, the computations may be performed for a subset of the frames and/or a subset of the voxels, wherein spatial and/or temporal interpolation and/or extrapolation may be used to estimate the compounding model PDF for any voxel. The interpolation and/or extrapolation may employ any method known in the art.

(c) An adaptive model ("adaptive compounding model"), wherein the compounding model PDF, i.e., the PDF for a voxel to be substantially affected (or substantially unaffected) by clutter effects as a function of the applicable compounding function parameter subset, is computed directly, without any prior assumptions regarding the shape of the PDF. The compounding model PDF may be computed using any method known in the art. For example, a one- or multi-dimensional histogram of the values of the applicable compounding function parameter subset for all relevant voxels may be calculated, wherein the histogram's dimensions should correspond to the number of parameters in the compounding function parameter subset. In order to adhere to the definition of a PDF, the histogram should be normalized such that the sum of all its elements would equal 1.0. If one assumes that:

(i) in most voxels, the primary source of the measured signal lies in a spatial angle close to the center of the mainlobe of the two-way beam pattern (this is because the beam pattern provides higher gain to this angular region, and most soft tissues have approximately the same reflective properties), and therefore voxels which are almost clutter free are also more ubiquitous than voxels which are strongly affected by clutter; and (ii) the compounding function parameter subset provides information regarding the local clutter levels and/or the angular direction of the primary source of the measured signal;

the result may be used as an estimate of the PDF for a voxel to be substantially unaffected by clutter effects. If one goes over each histogram element, and replaces its value by 1.0 minus the original value, the result may be used as an estimate of the PDF for a voxel to be substantially affected by clutter effects. Before computing the histogram, one may apply outlier rejection in one or more of its axes, i.e., for one or more of the parameters in the compounding function parameter subset, thus limiting the histogram's dynamic range. In some embodiments, the bins used in each histogram axis may be of a uniform width. In other embodiments, the bins used in one or more of the histogram axes may be of adaptive width, wherein narrower bin widths are allotted to regions with higher PDF values. In even further embodiments, Voronoi diagrams may be used instead of histograms.

In certain embodiments, the compounding model PDF may be computed using all relevant voxels in all frames at once. In other embodiments, the compounding model PDF may be computed separately for each frame and/or each group of voxels. In that context, groups of voxels may be separated in one or more of the scanned data array axes (e.g., different range swaths and/or different angular sections with respect to the broadside of the probe). In further embodiments, the compounding model PDF may be computed for a subset of the frames and/or a subset of the voxels, wherein spatial and/or temporal interpolation and/or extrapolation may be used to estimate the compounding model PDF for any voxel. The interpolation and/or extrapolation may utilize any method known in the art. For example, one may compute the compounding model PDF for the first frame out of every set of $N_f$ consecutive frames, and use that compounding model PDF for all $N_f$ consecutive frames.

Out of the three models, the predefined compounding model is expected to be most computationally efficient, but it cannot take into account medium-specific artifacts, e.g., local attenuation, scattering, refraction and diffraction effects, which may occur along the beam, changing its effective beam pattern. The adaptive compounding model is most accurate, yet it may be more computationally intensive. In order to reduce time complexity, one may use the compounding function implementation manners defined above.

In further embodiments, slight variations to the above described compounding models may allow one to produce normalized generalized metric values. As defined hereinabove, normalized generalized metrics are generalized metrics defined as real numbers whose value ranges from 0.0 to 1.0, wherein the value 0.0 is assigned to voxels that are substantially unaffected by clutter effects, and the value 1.0 is assigned to voxels in which substantially all of the measured signal emanates from clutter effects. As a result, for predefined compounding models, by correctly calibrating the predefined model one can obtain normalized generalized metrics instead of un-normalized generalized metrics. For simplified adaptive compounding models or adaptive compounding model, normalized generalized metrics may be obtained instead of un-normalized generalized metrics by utilizing the probability for a voxel to be substantially affected by clutter effects only (as a function of the applicable compounding function parameter subset) instead of the compounding model PDF.

The probability for a voxel to be substantially affected by clutter effects only ("compounding model probability function") may be derived from the compounding model PDF as follows:

Let $\{p_n\}$ be the compounding function parameter subset, $f_{PDF}(\{p_n\})$ be the compounding model PDF, and $P(\{p_n\})$ be the compounding model probability function.

For a compounding model PDF relating to the PDF for a voxel to be substantially affected by clutter effects only, $P(\{p_n\})$ for a given $\{p_n\}$ may be estimated by the sum over all values of $f_{PDF}(\{p_n\})$ in the model, which are lower than or equal to the value of $f_{PDF}$ for the specific $\{p_n\}$. In cases where $f_{PDF}(\{p_n\})$ is non-discrete, an integral should be used instead of a sum. Note that a PDF is by definition normalized so that its sum (or integral) over the entire model is 1.0, so that the compounding model probability function ranges from 0.0 to 1.0, as expected.

For a compounding model PDF relating to the PDF for a voxel to be substantially unaffected by clutter effects, $P(\{p_n\})$ for a given $\{p_n\}$ may be estimated by the sum over all values of $f_{PDF}(\{p_n\})$ in the model, which are higher than or equal to the value of $f_{PDF}$ for the specific $\{p_n\}$. In cases where $f_{PDF}(\{p_n\})$ is non-discrete, an integral should be used instead of a sum.

Beam Pattern Measurements

In some embodiments, the compounding model PDF and/or the compounding model probability function may be utilized for estimating the local beam pattern within a given medium, and/or features of that beam pattern, such as the width of the mainlobe in one or more axes. For instance, if the transmit beam pattern is common to a main receive beam and its associated auxiliary receive beams, the receive beam pattern and/or features of the receive beam pattern may be estimated. Appropriate models should be defined for that purpose, which may be theoretically determined and/or experimentally derived ("beam pattern measurement models").

For example, when using a single transmit beam, a single main receive beam and a single auxiliary receive beam, wherein the azimuth beam width of all beams is the same, but the elevation beam width of the main receive beam is lower than that of the transmit beam and the auxiliary receive beam, the compounding model PDF and/or the compounding model probability function are expected to contain information regarding the elevation beam width on receive. Similarly, when using a single transmit beam, a single main receive beam and two auxiliary receive beams— one wider than the main receive beam in azimuth only, and the other in elevation only, one may use each auxiliary receive beam separately in order to deduce information regarding the beam width on receive along the applicable axis.

In further embodiments, the generalized metric and/or the normalized generalized metric may be utilized to estimate the angular direction of the primary energy source of the signal measured on receive for one or more voxels in one or more frames, using beam pattern measurement models. For example, when using a single transmit beam, a single main receive beam and a single auxiliary receive beam, wherein the azimuth beam width of all beams is the same, but the elevation beam width of the main receive beam is lower than that of the transmit beam and the auxiliary receive beam, the generalized metric and/or the normalized generalized metric are expected to be indicative of the elevation angle from which most of the received energy originates for each voxel or each frame. Various configurations of transmit beams, main receive beams and/or auxiliary receive beams may be utilized for estimating the spatial angle of the main energy source for each voxel on receive.

Linear Compounding Functions

In some embodiments, the compounding function may be defined as a linear function of the local information for a main receive beam and one or more associated auxiliary receive beams. For example, if a single auxiliary receive beam is utilized, and a single normalized generalized metric m is calculated for each entry into the scanned data array $\vec{p}$ and/or each frame n separately (or for a subset of the entries into the scanned data array and/or for a subset of the frames), the compounding function may be defined as follows:

$$S_{out}(\vec{p},n) = [1 - m(\vec{p},n)] S_{main}(\vec{p},n) \qquad (3)$$

wherein $S_{main}$ is the local measured signal for the main receive beam, and $S_{out}$ is the clutter suppressed local signal. This equation attenuates the signal for clutter affected voxels, nullifying the signal for voxels in which substantially all of the measured signal emanates from clutter effects, whereas voxels determined to be clutter free are unaffected.

In other embodiments, if a single auxiliary receive beam is utilized, and a single normalized generalized metric is calculated for each entry into the scanned data array and each frame (or a subset thereof), the compounding function may be a linear combination of the local signal for the main receive beam, $S_{main}$, and the auxiliary receive beam, $S_{aux}$:

$$S_{out}(\vec{p},n) = S_{main}(\vec{p},n) - \tilde{W}(\vec{p},n) S_{aux}(\vec{p},n) \qquad (4)$$

wherein $\tilde{W}$ is a local complex weight ("clutter suppression weight"), which may be calculated for each entry into the scanned data array and/or each frame (or a subset thereof). The clutter suppression weight is computed so as to minimize the clutter contribution to $S_{out}$, whereas the relevant signal contribution is retained as much as possible.

If one normalizes the signal for the different auxiliary receive beams $S_{aux_i}$, where i is the auxiliary beam index, so that the gain of all auxiliary receive beams at the angular direction corresponding to that of the center of the main receive beam would match that of the main receive beam, to obtain normalized auxiliary receive beams, $\tilde{S}_{aux_i}$, one can relate to the signal emanating from the center of the main receive beam as the "clutter free" signal, $S_{free}$, and the remaining signal for each receive beam may be referred to as the clutter signal, denoted by $S_{main}^{clutter}$ for the main receive beam and $\tilde{S}_{aux_i}^{clutter}$ i'th normalized auxiliary receive beam:

$$S_{main}(\vec{p},n) = S_{free}(\vec{p},n) + S_{main}^{clutter}(\vec{p},n)$$

$$\tilde{S}_{aux_i}(\vec{p},n) = S_{free}(\vec{p},n) \tilde{S}_{aux_i}^{clutter}(\vec{p},n) \quad (5)$$

The clutter suppression weight should therefore be computed in such a way that $S_{out}$ would be as close as possible to $S_{free}$. Unlike the method in eq. (3), which significantly attenuates the signal in voxels where most of the measured signal emanates from clutter, this method may be able to extract relevant information from voxels in which clutter is the main source of the measured signal.

In order to simplify the description below, let us rewrite eq. (4) using normalized auxiliary receive beam signals:

$$S_{out}(\vec{p},n) = S_{main}(\vec{p},n) - W(\vec{p},n) \tilde{S}_{aux}(\vec{p},n) \quad (6)$$

wherein W is the local complex weight calculated using the normalized auxiliary receive beam signals.

When using eq. (6), the magnitudes and/or phases of $S_{out}$ may be skewed locally and/or globally. This is because the clutter suppression weight aims at nullifying clutter contributions, but as an adverse effect it also affects clutter free signals. For example, in a clutter free voxel, $S_{out}=(1-W) S_{free}$. In order to prevent these effects, a normalization factor may be introduces into eq. (6):

$$S_{out}(\vec{p},n) = \frac{S_{main}(\vec{p},n) - W(\vec{p},n)\tilde{S}_{aux}(\vec{p},n)}{1 - W(\vec{p},n)} \quad (7)$$

Special attention should be paid to voxels for which W approximately equals 1.0, so that eq. (7) may yield very high signal magnitudes due to "divide-by-zero" effects. For example, $S_{out}$ for such voxels may the defined as equaling $S_{main}$, so that the signal in such voxels remains unchanged. Alternatively, $S_{out}$ for such voxels may the set to the mean or median signal level of $S_{out}$ in the immediate vicinity of the current voxel, wherein the immediate vicinity may be defined in space and/or in time, and wherein voxels for which the value provided by eq. (7) has been replaced are excluded from the computation. Such techniques may also be used in other occurrences of "divide-by-zero" effects.

In embodiments, the clutter suppression weight for each applicable entry into the scanned data array $\vec{p}$ and/or each applicable frame n may be estimated as follows:

(a) Define a region surrounding $(\vec{p}, n)$, wherein the region may be spatial (i.e., including a set of near-by entries into the scanned data array) and/or temporal (i.e., including a set of consecutive frames, whose index is close to n) ("spatial-temporal region").

(b) Set the clutter suppression weight for $(\vec{p}, n)$ to be a function of at least one of:

(i) the values of one or more generalized metrics and/or normalized generalized metrics within the spatial-temporal region; and (ii) the local complex ratio between the signal for the main receive beam, $S_{main}$, and the signal in one of the normalized auxiliary receive beams, $\tilde{S}_{aux_i}$, within the spatial-temporal region ("local complex main-auxiliary ratio").

For example, the clutter suppression weight for $(\vec{p}, n)$ may be set to the local complex main-auxiliary ratio for to the voxel within the spatial-temporal region, whose generalized metric and/or normalized generalized metric values are most indicative of significant clutter effects. This exemplary function is based on the following assumptions:

(i) the clutter signal contribution changes slowly enough in space and/or in time, so that one may consider it to be approximately constant within small spatial-temporal regions; and (ii) speckle effects in ultrasonic imaging often cause local variations in the clutter free signal levels even for approximately homogeneous tissue regions, so that one may expect at least one of the voxels in the spatial-temporal region to include low free signal levels.

The voxel within the spatial-temporal region which is found to have the most substantial clutter effect may be treated as almost pure clutter, and therefore the local complex main-auxiliary ratio for that voxel is expected to significantly reduce the local clutter level. For further clarification, if we substitute $W(\vec{p}, n) \approx S_{main}^{clutter}(\vec{p}, n)/\tilde{S}_{aux_i}^{clutter}(\vec{p}, n)$ into eq. (7), we obtain $S_{out}(\vec{p}, n) \, S_{free}(\vec{p}, n)$.

(c) Special care should be taken to cases where the local complex main-auxiliary ratio is very high due to "divide-by-zero" effects. For example, in voxels where the computed clutter suppression weight is very high, one may replace it with a predefined value, e.g. 1.0 or 0.0. In the latter case, no clutter suppression will be applied to these voxels.

In further embodiments, one may compute a linear combination of the outputs of a compounding function and the main receive beam signal, wherein the weights are based on the normalized generalized metric. A potential benefit of this technique is reducing the effects of the compounding function on clutter free voxels. For example, if we base our method on eq. (7), we obtain:

$$S_{out}(\vec{p}, n) = [1 - m(\vec{p}, n)]S_{main}(\vec{p}, n) + \quad (8)$$
$$m(\vec{p}, n)\frac{S_{main}(\vec{p}, n) - W(\vec{p}, n)\tilde{S}_{aux}(\vec{p}, n)}{1 - W(\vec{p}, n)}$$

In even further embodiments, two or more normalized generalized metrics may be defined and utilized by the compounding function. For example, when using two normalized generalized metrics, m1 and m2, we can use the following equation, wherein for each applicable entry into the scanned data array and/or for each applicable frame, the sum of all coefficients is, by definition, 1.0:

$$S_{out}(\vec{p}, n) = [1 - m_1(\vec{p}, n)][1 - m_2(\vec{p}, n)]S_{main}(\vec{p}, n) + \quad (9)$$
$$m_1(\vec{p}, n)[1 - m_2(\vec{p}, n)]S_1(\vec{p}, n) + [1 - m_1(\vec{p}, n)]m_2(\vec{p}, n)S_2(\vec{p}, n) +$$
$$m_1(\vec{p}, n)m_2(\vec{p}, n)S_{1,2}(\vec{p}, n)$$

wherein $S_1$ and $S_2$ are the outputs of clutter suppression processes based on m1 and m2 respectively, applied using any method herein above; and $S_{1,2}$ is the output of a clutter suppression process based on both m1 and m2. This may be done, for example, by applying one of the above processes based on m1 to both the main receive beam and the auxiliary receive beams (i.e., each time a different beam is treated as the main receive beam), and then apply one of the above processes based on m2, substituting the receive beam signals in the appropriate equation with the corresponding outputs of the clutter suppression process based on m1. Alternatively, $S_{1,2}$ may be computed as a simple local statistical function of $S_1$ and $S_2$, e.g., local minimum (between $S_1$ and $S_2$), local average (between $S_1$ and $S_2$), and so forth.

In other embodiments, two or more normalized generalized metrics may be defined and utilized in the compounding function, wherein at least one normalized generalized metric is used directly and at least one normalized generalized metric is used to compute a clutter suppression weight. For example, when using two normalized generalized metrics, m1 and m2, wherein a clutter suppression weight W2 is computed using m2, the following equation may be used:

$$S_{out}(\vec{p}, n) = [1 - m_1(\vec{p}, n)][1 - m_2(\vec{p}, n)]S_{main}(\vec{p}, n) + \qquad (10)$$

$$m_2(\vec{p}, n) \frac{S_{main}(\vec{p}, n) - W_2(\vec{p}, n)\tilde{S}_{aux}(\vec{p}, n)}{1 - W_2(\vec{p}, n)}$$

Note that compounding functions defined as linear combinations of the local signal for the main receive beam and the auxiliary receive beam may be thought of in at least one of two ways:
(a) As algebraic expressions, designed to suppress clutter effects.
(b) As adaptive beam-forming schemes, designed to introduce nulls into the effective beam-pattern of the overall process, in directions corresponding to those of clutter sources.

It should be understood that the mathematical equations are provided as detailed examples only. Furthermore, even though the detailed examples refer to linear equations, non-linear equations may also be utilized.

Filtering of Generalized Metrics and/or Clutter Suppression Weights

Before utilizing a generalized metric and/or a normalized generalized metric for computing a clutter suppression weight and/or in a compounding function, it may undergo spatial filtering and/or temporal filtering. Similarly, before utilizing a clutter suppression weight in a compounding function, it may also undergo spatial filtering and/or temporal filtering. The filtering may be applied using the coordinate system of the scanned data array, wherein a time axis may be formed by combining the scanned data arrays collected in multiple frames, wherein consecutive frames are placed one alongside the other.

Any filter known in the art may be applied for that purpose. For example, a linear low-pass filter, band-pass filter of high-pass filter may be applied in one or more of the spatial axes and/or the time axis. Additionally or alternatively, non-linear filters such as a median filter may be applied in one or more of the spatial axes and/or the time axis. Such filters are expected to reduce local irregularities in the generalized metrics, normalized generalized metrics and/or clutter suppression weights.

Other non-linear filters, applied in one or more of the spatial axes and/or the time axis, may be considered. For example, one may use the local minimum, local maximum, local mean plus local standard deviation, local mean minus local standard deviation, a certain percentile of the local signal, and so on. When applied to a normalized generalized metric, a local minimum is expected to reduce misdetections of voxels as clutter affected, since the presence of voxels for which the normalized generalized metric value is low (i.e., voxels determined to include low clutter levels, and therefore mostly relevant information) also reduces the normalized generalized metric value in their immediate vicinity. Similarly, when applied to a normalized generalized metric, a local maximum is expected to increase the detection probability of clutter affected voxels, since the presence of voxels for which the normalized generalized metric value is high (i.e., voxels determined to include mostly clutter) also increases the normalized generalized metric value in their immediate vicinity.

Further, slightly more complex, non-linear filters may also be considered. For example, for each local region in space and/or time, the output of the non-linear filter may be produced as follows: if the local median or the local mean or the local weighted mean is higher than a predefined value, use a certain statistical operator, and otherwise—another statistical operator. Examples for such statistical operators are the local minimum, local maximum, local mean, local mean plus local standard deviation, local mean minus local standard deviation, a certain percentile of the local signal and so forth. Such filters, when applied to a normalized generalized metric, may allow one, for example, to increase the detection probability of clutter affected voxels in clutter affected regions and, at the same time, reduce the probability of misdetections in clutter free regions, assuming that clutter levels change relatively gradually in space and time.

Additionally or alternatively, a transfer function may be applied to a generalized metric and/or a normalized generalized metric and/or a clutter suppression weight in various stages of the clutter suppression process. Any transfer function known in the art may be used, with various purposes in mind. Transfer functions applied to a normalized generalized metric, which by definition ranges from 0.0 to 1.0, should preferably: (a) yield values between 0.0 and 1.0; and (b) for each pair of values, wherein the second value is higher than the first one, the result of the transfer function for the second value should be higher than or equal to the result of the transfer function for the first value.

For example, a transfer function may be applied to the normalized generalized metric m in eq. (3) and/or eq. (8) before using it for clutter suppression. Some exemplary transfer functions:
(a) Linear function with saturation; i.e., the transfer function is linear up to a predefined input value, and for higher input values—the output value is equal to that for the predefined input value.
(b) Logarithmic function.
(c) Exponential function.
(d) Sigmoid-like function.

Post-Processing

Before utilizing the output of a compounding function for any further computations, one may apply spatial and/or temporal processing to that output. The processing may be applied using the coordinate system of the scanned data array, wherein a time axis may be formed by combining the scanned data arrays collected in multiple frames, wherein consecutive frames are placed one alongside the other.

In some embodiments, the spatial and/or temporal processing may comprise of various spatial and/or temporal filters known in the art.

Additionally or alternatively, for each applicable entry into the scanned data array and/or each applicable frame, one may replace the output of the compounding function with the corresponding voxel of the main receive beam if a certain criterion is met. Alternatively, one may replace the local output of the compounding function with the mean signal, weighted mean signal or median signal within a small local region of the compounding function output, defined in space and/or in time.

For example, the local value of the output of a compounding function may be replaced by that of the corresponding voxel in the main receive beam if the local signal magnitude of the compounding function output is greater than the local signal magnitude of the main receive beam. Such a process may be considered, because the clutter suppression process is supposed to reduce clutter levels, without amplifying clutter free regions. For instance, high signal magnitudes may result from numerical effects such as "divide-by-zero."

Another exemplary post-process:
(a) Define a block within the scanned data array, centered or approximately centered at the current voxel ("data block"). Depending on the dimensions of the scanned data array (which may include spatial and potentially also temporal axes), said block may be 1D, 2D, 3D or four-dimensional (4D).
(b) For each of the main receive beam and the output of the compounding function, calculate the mean magnitude or the weighted mean magnitude within the data block, including or excluding the current voxel, and divide the result by the magnitude of the current voxel (alternatively, the mean magnitude in a smaller block within the scanned data array may be used).
(c) The value of the current voxel within the compounding function output should be replaced by that of the corresponding voxel in the main receive beam if the ratio between the output of the previous step for the main receive beam and for the output of the compounding function is higher-than (or lower-than) than a predefined constant. Alternatively, if the aforementioned criterion is met, the value of the current voxel within the compounding function output may be replaced by the mean signal, weighted mean signal or median signal within the data block of the compounding function output (either including or excluding the current voxel).

Such a post process may be used, for instance, in order to take care of small dark regions within the compounding function output, which appear in bright continuous (and larger) regions of the image.

Utilizing a Plurality of Main Receive Beams and/or a Plurality of Auxiliary Receive Beams In some embodiments, a plurality of main receive beams may be used concurrently, e.g., in MLA configurations. In such cases, one or more auxiliary receive beams may be defined, wherein each auxiliary receive beam is used in conjunction with one or more main receive beam.

In such cases, one possible clutter suppression method is to compute at least one of the following "compounding process functions":
(a) The compounding model PDF.
(b) The generalized metrics and/or normalized generalized metrics.
(c) The clutter suppression weights.
(d) The compounding function.

for each applicable entry into the scanned data array and/or each applicable frame employing each pair of main receive beam and associated auxiliary receive beam used ("main-auxiliary beam pair") separately.

Additionally or alternatively, one may define compounding model PDFs (or other compounding process functions) which are common to more than one main-auxiliary beam pair, e.g., for multiple main receive beams and one common auxiliary receive beam. In such cases, one may apply transformations to the data for each main-auxiliary beam pair within the group of pairs, which correspond to the estimated differences between various main-auxiliary beam pairs ("main-auxiliary beam pair data transformations"). For example:
(a) When using a simplified adaptive compounding model and/or an adaptive compounding model, wherein a single compounding model PDF ("common compounding model PDF") is used for multiple main-auxiliary beam pairs, one may apply a tailored transformation to the data from each main-auxiliary beam pairs before using it to produce the compounding model PDF ("main-auxiliary beam pair data transformation").
(b) When calculating the generalized metrics and/or normalized generalized metrics, the common compounding model PDF may be transformed for each main-auxiliary beam pair before using it for generalized metric and/or normalized generalized metric computation.

Examples for main-auxiliary beam pair data transformations, one or more of which may be used when adding information to the common compounding model PDF (similar but inverse transformation may be employed when using the common compounding model PDF values for generalized metric and/or normalized generalized metric calculations):
(a) Before adding information based on a given main-auxiliary beam pair to the common compounding model PDF, a constant may be added to one or more of the information's components, corresponding to one or more of the compounding function parameters referred to by the compounding model PDF. This transformation is referred to as translation of the compounding model PDF. For example, if two or more main receive beams and one auxiliary receive beam are used, wherein the beam patterns of the main receive beams are identical except for spatial rotation about the phase center of the transducer array, one may expect that the compounding model PDF calculated for each of the two or more main-auxiliary beam pairs would be similar, but translated in one or more of the compounding function parameters referred to by the compounding model PDF.
(b) Before adding information based on a given main-auxiliary beam pair to the common compounding model PDF, either a linear or a non-linear transformation may be applied to one or more of the information's components, corresponding to one or more of the compounding function parameters referred to by the compounding model PDF. The linear or non-linear transformation may be applied to one or more compounding function parameters separately, but it may also be applied to two or more of the compounding function parameters combined. For example, if two or more main receive beams and one auxiliary receive beam are used, wherein the beam patterns of the mainlobes of all main receive beams point at the same direction, but their beam widths are different, one may expect that the compounding model PDF calculated for each of the two or more main-auxiliary beam pairs would be similar, but stretched/compressed along one or more of the compounding function parameters referred to by the compounding model PDF.

In further embodiments, a plurality of auxiliary receive beams may be used concurrently, either with a single main receive beam or with a plurality of main receive beams. One or more of the following techniques may be employed is such cases:

(a) One or more of the aforementioned clutter suppression schemes may be applied for each main-auxiliary beam pair separately. After that, for each applicable small spatial volume and/or for each applicable frame, a function may be applied to clutter suppression outputs for one or more of the associated main-auxiliary beam pairs ("multi-pair combining function"). Any function known in the art may be used, e.g., mean, maximum, minimum, median, a predefined percentile, weighted sum and so forth. For ordinal operators such as the median, the operator computation should be based on sorting the relevant values according to their magnitudes. The multi-pair combining function may also take into account one or more generalized metrics and/or normalized generalized metrics, as computed for one or more of the main-auxiliary beam pairs, e.g., a weighted sum may be calculated, wherein higher weights are assigned to values for main-auxiliary beam pairs in which the signal is considered to include lower clutter levels.

(b) For each applicable small spatial volume and/or for each applicable frame, one or more of the aforementioned clutter suppression schemes may be applied for a specific main-auxiliary beam pair. The clutter suppression output may then be referred to as a new (synthetic) main or auxiliary receive beam, to be used in conjunction with another auxiliary and/or main receive beam as inputs to one or more of the above described clutter suppression schemes. This process may be iteratively repeated several times.

(c) For each applicable small spatial volume and/or for each applicable frame, a compounding function may be applied to a main receive beams and a plurality of auxiliary receive beams, to produce a clutter suppressed output, wherein the compounding function employs one or more clutter suppression weights. For example, if we extend eq. (6) to relate to multiple auxiliary receive beams, we obtain:

$$S_{out}(\vec{p},n) = S_{main}(\vec{p},n) - \Sigma_m W_m(\vec{p},n)\tilde{S}_{aux_m}(\vec{p},n) \quad (11)$$

Similar equations may be written for any of the other clutter suppression methods described herein.

The weight vector $W_m$ in eq. (11), or similar coefficients in other clutter suppression equations referring to multiple auxiliary receive beam, may be estimated using any technique known in the art. For example, one may employ mean-square-error optimization, that is, for eq. (11), the weight vector $W_m$ for each applicable small spatial and/or temporal region may be set so as to minimize the expectation value of the output signal power, that is, $E[|S_{main}(\vec{p}, n)\Sigma_m W_m(\vec{p}, n)\tilde{S}_{aux_m}(\vec{p}, n)|^2]$, wherein E is the expectation operator.

Another example would be to compute the weight vector $W_m$ in eq. (11), or similar coefficients in other clutter suppression equations referring to multiple auxiliary receive beam, for each main-auxiliary beam pair separately, without taking the other main-auxiliary beam pairs into account. This methodology may be useful, for example, when the mainlobe of the main receive beam and the one or more auxiliary receive beams point at the same spatial direction, and for each main-auxiliary beam pair the beam width of the main and auxiliary receive beams are the same along a certain direction but different along another direction, wherein the directions along with the beams have different widths in different main-auxiliary beam pairs may or may not be perpendicular. In such cases, different main-auxiliary beam pairs may be utilized to suppress clutter originating from different spatial angles with respect to the mainlobe of the main receive beam.

(d) For each applicable small spatial volume and/or for each applicable frame, a compounding function may be applied to a main receive beams and a plurality of auxiliary receive beams, to produce a clutter suppressed output, wherein the compounding function is linear, but does not employ clutter suppression weights, for instance, as described in eq. (3). In this case, the generalized metric and/or normalized generalized metric may be based on compounding function parameters which relate to more than one auxiliary receive beam associated with one or more main receive beams. For example, when using two auxiliary receive beams associated with a single main receive beam, one may use the following compounding function parameters:
  (i) the local relative magnitude between the main receive beam and the first auxiliary receive beam;
  (ii) the local phase difference between the main receive beam and the first auxiliary receive beam;
  (iii) the local relative magnitude between the main receive beam and the second auxiliary receive beam; and
  (iv) the local phase difference between the main receive beam and the second auxiliary receive beam.

(e) For each applicable small spatial volume and/or for each applicable frame, a compounding function may be applied to a main receive beams and a plurality of auxiliary receive beams, to produce a clutter suppressed output, wherein:
  (i) the compounding function employs one or more clutter suppression weights; and
  (ii) one or more of the generalized metrics and/or normalized generalized metrics may be based on compounding function parameters which relate to more than one auxiliary receive beam associated with one or more main receive beams.

(f) For each applicable small spatial volume and/or for each applicable frame, a compounding function may be applied to a main receive beams and a plurality of auxiliary receive beams, to produce a clutter suppressed output, wherein any compounding function may be employed.

As noted herein above, one or more receive beams may be employed as both main receive beams and as auxiliary receive beams, within the context of different main-auxiliary beam pairs.

Utilizing Main and Auxiliary Receive Beams Having Different Phase Centers

In some embodiments, for each main receive beam, the phase centers of all associated auxiliary receive beams are identical to that of the corresponding main receive beam. In other embodiments, there is at least one main-auxiliary beam pair for which the main and auxiliary receive beams have different phase centers ("non-concentric main-auxiliary beam pair").

An exemplary use for such configurations is suppression of reverberation effects, in addition to sidelobe clutter effects. Reverberation artifacts measured for different receive phase centers are expected to be different, so that compounding functions may suppress both sidelobe clutter and reverberations.

In non-concentric main-auxiliary beam pairs, the scanned data array associated with the auxiliary receive beam may be translated and/or rotated with respect to the scanned data array associated with the corresponding main receive beam.

In certain embodiments, spatial registration may be applied between the scanned data arrays associated with the main and auxiliary receive beams in non-concentric main-auxiliary beam pair ("main-auxiliary beam pair registration"). The registration may be performed for the entire cine-loop, for each frame separately, in each frame—for each entry into the scanned data array or group of adjacent entries, or for each entry into the scanned data array or group of adjacent entries in the entire cine-loop. The spatial registration may be performed using any technique known in the art. In some cases, the spatial registration may be rigid, accounting for global translations and/or global rotation. Additionally or alternatively, the spatial registration may be non-rigid, also taking into account local deformations resulting from physical effects within the medium. In certain cases, some translation parameters, such as the global translation and the global rotation, may be directly derived from the relative geometry of the centerlines of the main and auxiliary receive beams, which are known and controllable. Additionally or alternatively, some translation parameters may be initially estimated according to the relative geometry of the centerlines of the main and auxiliary receive beams, and then fine-tuned according to the respective acquired scanned data arrays.

In non-concentric main-auxiliary beam pairs, the spatial angle between the center of a voxel and the centerline of the main receive beam ("main spatial angle") is typically different than the spatial angle between the center of said voxel and the centerline of the respective auxiliary receive beam ("auxiliary spatial angle"). Moreover, the difference between the main spatial angle and the auxiliary spatial angle may be different for different voxels. As a result, the local relative magnitude and/or the local phase difference between the main and the auxiliary receive beam, as calculated for reflectors along the centerline of the main receive beam, may change as a function of range ("parameter range variability"). In certain embodiments, the compounding function may be adjusted in order to handle this parameter range variability. For example, one may utilize main-auxiliary beam pair data transformations, as defined hereinabove, wherein the transformation for some voxels may be derived from the main spatial angle and auxiliary spatial angle for each voxel or group of voxels, wherein the main spatial angles and auxiliary spatial angles may be computed based on the geometric location of the center of the voxel with respect to the phase centers of the main and auxiliary receive beams, and/or from the outputs of the main-auxiliary beam pair registration process, if applied.

Clutter Suppression Based on Both Clutter De-Correlation Times and Spatial-Temporal Analysis U.S. Pat. No. 8,045,777, also referenced herein above, describes a clutter suppression method based on computing a linear combination of the signals in a main receive beam and in one or more auxiliary receive beams, wherein the coefficients of the linear combination ("temporal clutter suppression weights") are computed so as to suppress reflections due to clutter, wherein a reflection is determined as associated with clutter if the determined de-correlation time is above a specified threshold ("temporal clutter suppression process"). When a single auxiliary receive beam is associated with each main receive beam, the following equation may be used:

$$S_{out}(\vec{p},n) = S_{main}(\vec{p},n) - W_t(\vec{p},n)\tilde{S}_{aux}(\vec{p},n) \quad (12)$$

wherein the complex weight $W_t$ for each applicable entry into the scanned data array $\vec{p}$ and/or each applicable frame n is computed as follows:

$$W_t(\vec{p}, n) = \frac{F_t[S_{main}(\vec{p}, n)]}{F_t[\tilde{S}_{aux}(\vec{p}, n)]} \quad (13)$$

where Ft is a temporal low-pass filter, applied for each applicable entry into the scanned data array and/or each applicable frame.

This technique may be combined with the clutter suppression techniques hereof, using compounding functions which also depend on temporal clutter suppression weights. For example, one or more generalized metrics and/or normalized generalized metrics may be used in addition to one or more temporal clutter suppression weights, as can be seen in the following exemplary equation:

$$S_{out}(\vec{p}, n) = [1 - m_1(\vec{p}, n)]S_{main}(\vec{p}, n) + \quad (14)$$
$$m(\vec{p}, n)\frac{S_{main}(\vec{p}, n) - W_t(\vec{p}, n)\tilde{S}_{aux}(\vec{p}, n)}{1 - W_t(\vec{p}, n)}$$

wherein m is a normalized generalized metric, used so as to adjust the effect of the temporal clutter suppression process in each voxel based on the estimated local clutter contribution.

The invention claimed is:

1. A method of ultrasound imaging, said method comprising:
   transmitting ultrasound radiation towards a target and receiving reflections of the ultrasound radiation from a region of the target in a main reflected signal and one or more auxiliary reflected signals, wherein each one of the reflected signals comprises an input dataset and is associated with a beam with a different and distinct beam pattern;
   compounding the input datasets from the main reflected signal and one or more auxiliary reflected signals, by the use of a compounding function, said compounding function using parameters derived from spatial analysis of the input datasets, said compounding function parameters being derived from at least one of:
   (a) A local phase difference and/or magnitude difference and/or magnitude ratio and/or complex signal ratio between difference receive beams, and/or functions of one or more of the aforementioned parameters;
   (b) Spatial functions of the local phase difference and/or magnitude difference and/or magnitude ratio and/or complex signal ration between difference beams;
   (c) A local difference and/or ratio between spatial functions of the local magnitude and/or phrase and/or complex signal in the different receive beams;
   (d) Applying multiple temporal band-pass filters to the local magnitude and/or phase and/or complex signal in the different receive beams, applying spatial analysis to the outputs of multiple temporal band-pass filters and compounding the results;
   (e) Applying multiple temporal band-pass filters to the local phase difference and/or magnitude difference and/or magnitude ratio and/or complex signal ratio between different receive beams, applying spatial analysis to the outputs of multiple temporal band-pass filters and compounding the results; or (f) Spatial-temporal functions of the local phase difference and/or magnitude difference and/or magnitude ratio between different beams, wherein spatial derivatives of the local phase difference and/or magnitude difference and/or magnitude ratio between different beams, are applied after local temporal filtering; or wherein the local difference and/or ratio between spatial functions of the magnitude and/or phase and/or complex signal in the different beams are applied after local temporal filtering, wherein the compounding function parameter is a generalized metric and is indicative of the probability for the corresponding voxel to be substantially affected by clutter effects only, as derived using certain physical and/or physiologic assumptions, wherein the generalized metric is a normalized generalized metric and is defined as real numbers whose values range from 0.0 to 1.0, wherein the value 0.0 is assigned tovoxels that are substantially unaffected by clutter effects, and the value 1.0 is assigned to voxels in which substantially all of the measured signal emanates from clutter effects, and wherein the normalized generalized metric is the estimated probability for the corresponding voxel to be substantially affected by clutter effects only, and wherein the compounding function is defined as a linear function of the local information for a main reflected beam and one or more associated auxiliary beams and wherein the compounding function is defined by the following equation:

$S_{out} = [1-m]S_{main}$ wherein m is the normalized generalized metric; $S_{main}$ is the local measured signal for the main reflected beam; and $S_{out}$ is the clutter suppressed local signal.

2. The method of claim 1, wherein the output of the compounding function for any region of the target in any time frame may be used instead of the measured main reflected signal in any further processing performed by ultrasound scanners, said further processing being at least one of:

(a) Log-compression;
(b) Time-gain control;
(c) Global gain control; or
(d) Doppler processing, wherein said Doppler processing is one of: color-Doppler flow imaging; tissue-Doppler imaging; pulse-Doppler studies; and/or continuous-wave Doppler studies.

3. The method of claim 1, wherein the main reflected signal and the one or more auxiliary reflected signals result from a single transmitted pulse or from two or more transmitted pulses.

4. The method of claim 1, wherein the main reflected signal and the one or more auxiliary reflected signals are obtained in one of the following ways:

(a) All obtained concurrently, wherein the main reflected signal and the one or more auxiliary reflected signals are all associated with the same transmit pulse;
(b) All obtained at different times, wherein each of the main reflected signal and the one or more auxiliary reflected signals is associated with a different transmit pulse; or
(c) Divided into groups of reflected signals, wherein each group of reflected signal may comprise a main reflected signal and/or one or more auxiliary reflected signals, wherein each group of reflected signals is obtained concurrently but different groups are obtained at different times, and wherein each group of reflected signals is associated with a different transmit pulse.

5. The method of claim 1, wherein the local phase difference and/or magnitude difference and/or magnitude ratio are indicative of the angular direction of the signal source.

6. The method of claim 1, wherein for non-clutter signals which originate from angular directions approximately corresponding to the center of the mainlobe of the beam associated with the main reflected signal, the signal level and/or the magnitude of the signal level change as a function of spatial location approximately the same way in the main reflected signal and in the one or more auxiliary reflected signals, wherein the change as a function of spatial location is defined by at least one of: the local signal level; the local spatial derivatives; and the local normalized spatial derivatives, said local normalized spatial derivative being defined by the local spatial derivative divided by the local signal.

7. The method of claim 1, wherein temporal filters are employed to estimate the signal levels for target elements with predefined dynamic properties.

8. The method of claim 1, wherein the dataset collected by one or more reflected signals, in each time-swath or frame, is organized in a 1D, 2D or 3D scanned data array and the compounding function parameter is computed for a predefined subset of the frames, and in each frame, for each entry into the scanned data array or group of adjacent entries, and applied to all frames, wherein the parameters applied in a specific frame are the ones computed for the closest frame index, or alternatively, the closest frame index which is equal to or lower than the current frame index.

9. The method of claim 8, wherein spatial interpolation and/or interpolation in time is used in order to derive the compounding function parameters applied in a given frame.

10. The method of claim 1, wherein the generalized metric for a set of voxels in a set of frames is derived using the following four-step process:

(a) Select one or more compounding function parameters to be used (compounding function parameter set) from the following parameters:

(i) parameter #1: the local magnitude ratio between two different reflected beams (a main and an auxiliary beam);
parameter #2: the local phase difference between two different reflected beams;

(ii) parameter #1: the local ratio of spatial magnitude derivatives along a first spatial axis between two different reflected beams;
parameter #2: the local ratio of spatial magnitude derivatives along a second spatial axis between two different reflected beams;

(iii) parameter #1: the local ratio of normalized spatial magnitude derivatives along a first spatial axis between two different reflected beams;
parameter #2: the local ratio of normalized spatial magnitude derivatives along a second spatial axis between two different reflected beams;
wherein a normalized local signal derivative is defined as the local signal derivative divided by the local signal;

(iv) parameter #1: the ratio of local magnitude spatial derivatives between two different receive beams, wherein the spatial derivative is computed using a "Laplacian filter";

parameter #2 : the local magnitude ratio between two different beams;
(v) parameter #1: the ratio of local normalized magnitude spatial derivatives between two different reflected beams, wherein the normalized spatial derivative is computed by dividing the local output of a "Laplacian filter" (applied to the local signal magnitude) by the local signal magnitude;
parameter #2: the local magnitude ratio between two different reflected beams; and
(vi) parameter #1: the ratio of the normalized magnitude spans between two different reflected beams, wherein a normalized magnitude span is defined as the difference between the maximal and minimal magnitudes (with or without outlier rejection) within a local region, divided by the mean magnitude in said region, wherein the local region is defined so that its width is greater than its height;
parameter #2: the ratio of the normalized magnitude spans between two different beams, wherein the local region is defined so that its height is greater than its width;
(b) Define a model for at least one of:
(i) the probability (or a simple function thereof, such as the probability density function) for a voxel to be substantially affected by clutter effects only;
(ii) the probability (or a simple function thereof, such as the probability density function) for a voxel to be substantially unaffected by clutter effects; and
(iii) the percentage of the energy within the corresponding voxel that originates from clutter effects (or a simple function thereof);
as a function of the compounding function parameter set values or the values for a subset of the compounding function parameter set (compounding model);
(c) Compute the compounding function parameter set for each relevant voxel and/or its immediate vicinity, said immediate vicinity being defined in space and/or in time;
(d) For each relevant voxel, use the one or more compounding models to estimate at least one of the following (or a simple function thereof):
(i) the probability for its being substantially affected by clutter effects only;
(ii) the probability for its being substantially unaffected by clutter effects; and
(iii) the percentage of the energy within the corresponding voxel that originates from clutter effects.

11. The method of claim 1, wherein the compounding function parameter is a generalized metric, wherein a compounding function parameter set is a set of one or more compounding function parameters to be used, wherein a compounding function parameter subset is either a subset or a full set of a compounding function parameter set, wherein a compounding model is a model of at least one of:
(i) the probability (or a simple function thereof, such as the probability density function) for a voxel to be substantially affected by clutter effects only;
(ii) the probability (or a simple function thereof, such as the probability density function) for a voxel to be substantially unaffected by clutter effects; and
(iii) the percentage of the energy within the corresponding voxel that originates from clutter effects (or a simple function thereof);
as a function of the compounding function parameter set values or the values for a subset of the compounding function parameter set, and wherein the compounding model may be defined in one of more of the following ways:
(a) A predefined model, which may be theoretically determined and/or experimentally derived;
(b) A simplified adaptive model, based on an assumption regarding the shape of the probability density function for a voxel to be substantially affected (or substantially unaffected) by clutter effects as a function of the applicable compounding function parameter subset (compounding model probability density function);
(c) An adaptive model, wherein the compounding model probability density function is computed directly, without any prior assumptions regarding the shape of the probability density function.

12. The method of claim 11, wherein voxels that are substantially unaffected by clutter are assumed to be more ubiquitous than voxels that are strongly affected by clutter.

13. The method of claim 11, wherein the compounding function parameter subset provides information regarding the local clutter levels and/or the angular direction of the primary source of the measured signal energy.

14. The method of claim 11, wherein the compounding model probability density function is computed using all relevant voxels in all frames at once.

15. The method of claim 11, wherein the dataset collected by one or more reflected signals, in each time-swath or frame, is organized in a 1D, 2D or 3D scanned data array, and wherein the compounding model probability density function is computed separately for each frame and/or each group of voxels, wherein the groups of voxels are separated in one or more scanned data array axes.

16. The method of claim 11, wherein the compounding model probability density function is utilized for estimating the local beam pattern within a given target region, and/or features of that beam pattern.

17. A method of ultrasound imaging, said method comprising:
transmitting ultrasound radiation towards a target and receiving reflections of the ultrasound radiation from a region of the target in a main reflected signal and one or more auxiliary reflected signals, wherein each one of the reflected signals comprises an input dataset and is associated with a beam with a different and distinct beam pattern;
compounding the input datasets from the main reflected signal and one or more auxiliary reflected signals, by the use of a compounding function, said compounding function using parameters derived from spatial analysis of the input datasets, said compounding function parameters being derived from at least one of:
(a) A local phase difference and/or magnitude difference and/or magnitude ratio and/or complex signal ratio between different receive beams, and/or functions of one or more of the aforementioned parameters;
(b) Spatial functions of the local phase difference and/or magnitude difference and/or magnitude ratio and/or complex signal ratio between different beams;
(c) A local difference and/or ratio between spatial functions of the local magnitude and/or phase and/or complex signal in the different receive beams;
(d) Applying multiple temporal band-pass filters to the local magnitude and/or phase and/or complex signal in the different receive beams, applying spatial analysis to the outputs of multiple temporal band-pass filters and compounding the results;
(e) Applying multiple temporal band-pass filters to the local phase difference and/or magnitude difference and/ or magnitude ratio and/or complex signal ratio between different receive beams, applying spatial analysis to the outputs of multiple temporal band-pass filters and compounding the results; or (f) Spatial-temporal functions of the local phase difference and/or magnitude difference and/or magnitude ratio between different beams, wherein spatial derivatives of the local phase difference and/or magnitude difference and/or magnitude ratio between different beams, are applied after local temporal filtering; or wherein the local difference and/or ratio between spatial functions of the magnitude and/or phase and/or complex signal in the different beams are applied after local temporal filtering, wherein the compounding function parameter is a generalized metric and is indicative of the probability for the corresponding voxel to be substantially affected by clutter effects only, as derived using certain physical and/or physiologic assumptions, wherein the generalized metric is a normalized generalized metric and is defined as real numbers whose values range from 0.0 to 1.0, wherein the value 0.0 is assigned to voxels that are substantially unaffected by clutter effects, and the value 1.0 is assigned to voxels in which substantially all of the measured signal emanates from clutter effects, and wherein the normalized generalized metric is the estimated probability for the corresponding voxel to be substantially affected by clutter effects only, and wherein the compounding function is computed by a linear combination of the outputs of another compounding function and the main reflected beam signal, wherein the weights are based on a normalized generalized metric, and wherein the compounding function is defined by the following equation:

$$S_{out}[1-m]S_{main} + m\frac{S_{main} - W\tilde{S}_{aux}}{1-W}$$

wherein $S_{main}$ is the local measured signal for the main reflected beam; $S_{out}$ is the local measured signal for an auxiliary beam, normalized so that the gain of the auxiliary beam at an angular direction corresponding to the center of the main receive beam would match that of the main receive beam; m is a normalized generalized metric; $S_{out}$ is the clutter suppressed local signal; and w is a local complex weight (clutter suppression weight), which may be calculated for each voxel and/or each frame or a subset thereof.

18. The method of claim 17, wherein the clutter suppression weight for each applicable voxel $\vec{p}$ and/or each applicable frame n is estimated by the following steps:

(a) Define a region surrounding ($\vec{p}$, u), wherein the region may be spatial and/or temporal (spatial-temporal region);

(b) Set the clutter suppression weight for ($\vec{p}$, n) to be a function of at least one of:
(i) the values of one or more generalized metrics and/or normalized generalized metrics within the spatial-temporal region; and
(ii) the local complex ratio between the signal for the main receive beam, and the signal in one of the normalized auxiliary receive beams, within the spatial-temporal region (local complex main-auxiliary ratio).

19. The method of claim 18, wherein the clutter suppression weight for ($\vec{p}$, n) is set to the local complex main-auxiliary ratio for the voxel within the spatial-temporal region, whose generalized metric and/or normalized generalized metric values are most indicative of significant clutter effects;

wherein the computation of the clutter suppression weight is based on the following assumptions:
(a) The clutter signal contribution changes slowly enough in space and/or in time, such that it is approximately constant within small spatial-temporal regions; and
(b) Speckle effects in ultrasonic imaging cause local variations in the clutter free signal levels even for approximately homogeneous tissue regions, such that one may expect at least one of the voxels in the spatial-temporal region to include low free signal levels.

20. The method of claim 1, wherein the dataset collected by one or more reflected signals, in each time-swath or frame, is organized in a 1D, 2D or 3D scanned data array, wherein at least one of the following post-processing steps is applied to the output of the compounding function:

(a) For each applicable entry into the scanned data array and/or each applicable frame, replace the output of the compounding function with the corresponding voxel of the main receive beam if a certain criterion is met;
(b) For each applicable entry into the scanned data array and/or each applicable frame, replace the local output of the compounding function with the mean signal, weighted mean signal or median signal within a small local region of the compounding function output, defined in space and/or in time; and
(c) For each applicable entry into the scanned data array and/or each applicable frame (current voxel), apply the following process:
(i) Define a block within the scanned data array, approximately centered at the current voxel (data block), wherein said block may be one-dimensional, two-dimensional, three dimensional or four-dimensional;
(ii) For each of the main receive beam and the output of the compounding function, calculate the mean magnitude or the weighted mean magnitude within the data block, including or excluding the current voxel, and divide the result by the magnitude of the current voxel or by the mean magnitude in a smaller block within the scanned data array; and
(iii) Replace the value of the current voxel within the compounding function output by one of: the value of the corresponding voxel in the main receive beam, the mean signal, weighted mean signal or median signal within the data block of the compounding function output; if the ratio between the output of step (ii) for the main receive beam and for the output of the compounding function is higher-than or lower-than than a predefined constant.

21. The method of claim 1, wherein a plurality of main receive beams are used concurrently, and wherein at least one of the following:
(a) A compounding model probability density function;
(b) A generalized metric and/or a normalized generalized metric;
(c) A clutter suppression weight; and
(d) The compounding function;
is computed in at least one of the following ways:

(i) Employing each pair of main receive beam and associated auxiliary receive beam used (main-auxiliary beam pair) separately; and
(ii) Once for at least two main-auxiliary beam pairs, wherein transformations are applied to data relating to each main-auxiliary beam pair.

22. The method of claim 1, wherein the input datasets from the main reflected signal and the one or more auxiliary reflected signals are in one of the following forms:
    (a) Analog signal; or
    (b) Digital signal.

23. The method of claim 1, wherein the input datasets from the main reflected signal and the one or more auxiliary reflected signals are in one of the following forms:
    (a) Real representation; or
    (b) Complex representation.

24. The method of claim 1, wherein the input datasets from the main reflected signal and the one or more auxiliary reflected signals are taken from at least one of the following processing phases of ultrasound scanners:
    (a) Before matched filtering and before down-conversion;
    (b) Before matched filtering but after down-conversion;
    (c) After matched filtering but before down-conversion;
    (d) After matched filtering and after down-conversion.

* * * * *